US011906563B2

(12) United States Patent
Kimizuka

(10) Patent No.: US 11,906,563 B2
(45) Date of Patent: Feb. 20, 2024

(54) ELECTRIC POTENTIAL MEASURING DEVICE AND METHOD FOR MANUFACTURING ELECTRIC POTENTIAL MEASURING DEVICE

(71) Applicant: SONY SEMICONDUCTOR SOLUTIONS CORPORATION, Kanagawa (JP)

(72) Inventor: Naohiko Kimizuka, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 525 days.

(21) Appl. No.: 17/250,183

(22) PCT Filed: Jun. 12, 2019

(86) PCT No.: PCT/JP2019/023178
§ 371 (c)(1),
(2) Date: Dec. 10, 2020

(87) PCT Pub. No.: WO2019/244726
PCT Pub. Date: Dec. 26, 2019

(65) Prior Publication Data

US 2021/0172990 A1 Jun. 10, 2021

(30) Foreign Application Priority Data

Jun. 19, 2018 (JP) ................................ 2018-116172

(51) Int. Cl.
*G01R 29/12* (2006.01)
*G01N 27/30* (2006.01)
*G01N 27/416* (2006.01)

(52) U.S. Cl.
CPC .......... *G01R 29/12* (2013.01); *G01N 27/301* (2013.01); *G01N 27/416* (2013.01)

(58) Field of Classification Search
CPC .... G01R 29/12; G01N 27/301; G01N 27/416; G01N 27/3277; C12M 1/00; C12M 1/34
See application file for complete search history.

(56) References Cited

U.S. PATENT DOCUMENTS 6,093,074 A * 7/2000 Suzuki .................... H01J 9/025 445/51
6,132,683 A * 10/2000 Sugihara ............... C12M 41/46 204/403.01

(Continued)

FOREIGN PATENT DOCUMENTS

CN 1383487 A 12/2002
CN 102401777 A 4/2012

(Continued)

OTHER PUBLICATIONS

International Search Report and Written Opinion of PCT Application No. PCT/JP2019/023178, dated Aug. 13, 2019, 14 pages of ISRWO.

*Primary Examiner* — Akm Zakaria
(74) *Attorney, Agent, or Firm* — CHIP LAW GROUP

(57) ABSTRACT

To provide an electric potential measuring device that can further improve evaluation quality. Provided is an electric potential measuring device including a plurality of readout electrodes arranged in an array form and each configured to detect an electric potential of an action potential generation point generated by an action of a cell, an insulating member, a reference electrode configured to detect a reference potential, and an amplification section configured to obtain a potential difference between a detected electric potential based on the readout electrode and a detected electric potential based on the reference electrode, in which the readout electrode has a covered region where the insulating member is stacked on the readout electrode and an opened region where the insulating member is not stacked on the (Continued)

readout electrode, and the readout electrode has, in the opened region, at least one high portion with high height and/or at least one low portion with low height, with a stacking surface of the readout electrode with the insulating member as a standard.

12 Claims, 8 Drawing Sheets

(56) References Cited

U.S. PATENT DOCUMENTS

2002/0113607 A1 8/2002 Yukimasa
2004/0209352 A1* 10/2004 Ozaki .................... C12Q 1/001 435/287.1
2009/0000957 A1* 1/2009 Dubin ............... B01L 3/502715 205/688
2011/0209899 A1 9/2011 Hill
2012/0048737 A1 3/2012 Yamaguchi et al.
2012/0048739 A1 3/2012 Choi et al.
2014/0035139 A1 2/2014 Kato
2015/0153302 A1* 6/2015 Davis ....................... C12M 1/34 204/403.08
2018/0348161 A1 12/2018 Ogi et al.

FOREIGN PATENT DOCUMENTS

CN 108291887 A 7/2018
JP 2002-031617 A 1/2002
JP 2011-069727 A 4/2011
JP 2012-047536 A 3/2012
JP 2012-052839 A 3/2012
JP 2014-033105 A 2/2014
WO 2017/061171 A1 4/2017

* cited by examiner

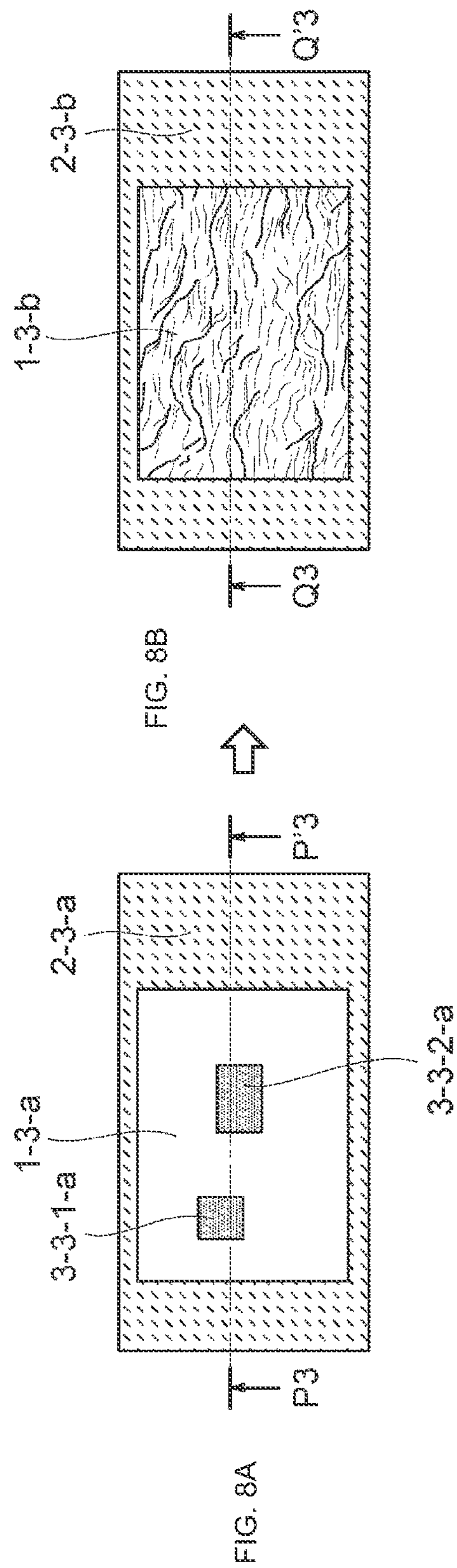
FIG. 8A
FIG. 8B
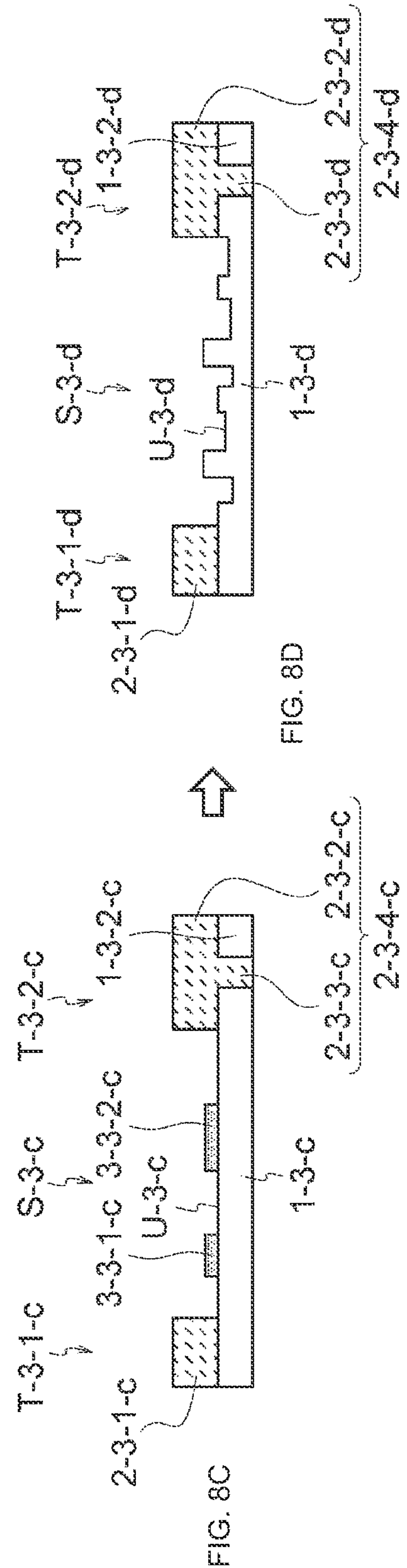
FIG. 8C
FIG. 8D

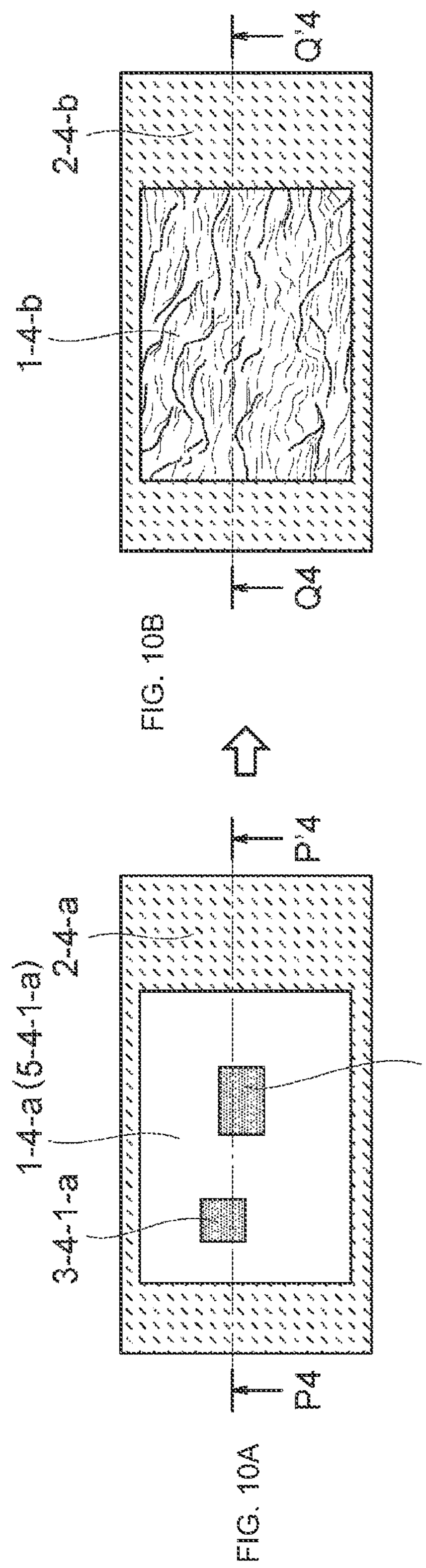
FIG. 10A
3-4-1-a
1-4-a(5-4-1-a)
2-4-a
3-4-2-a
P4
P'4
FIG. 10B
1-4-b
2-4-b
Q4
Q'4
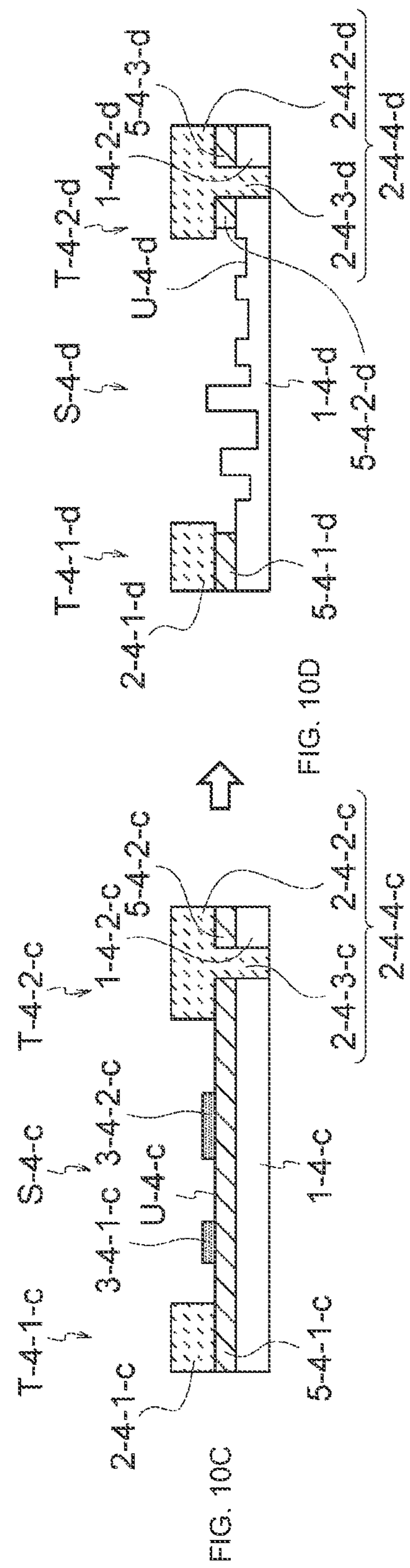
FIG. 10C
2-4-1-c
T-4-1-c
3-4-1-c
S-4-c
U-4-c
3-4-2-c
T-4-2-c
1-4-2-c
5-4-2-c
2-4-3-c
2-4-2-c
2-4-4-c
1-4-c
5-4-1-c
FIG. 10D
2-4-1-d
T-4-1-d
S-4-d
U-4-d
T-4-2-d
1-4-2-d
5-4-3-d
2-4-3-d
2-4-2-d
2-4-4-d
1-4-d
5-4-2-d
5-4-1-d

ELECTRIC POTENTIAL MEASURING DEVICE AND METHOD FOR MANUFACTURING ELECTRIC POTENTIAL MEASURING DEVICE

CROSS REFERENCE TO RELATED APPLICATIONS

This application is a U.S. National Phase of International Patent Application No. PCT/JP2019/023178 filed on Jun. 12, 2019, which claims priority benefit of Japanese Patent Application No. JP 2018-116172 filed in the Japan Patent Office on Jun. 19, 2018. Each of the above-referenced applications is hereby incorporated herein by reference in its entirety.

TECHNICAL FIELD

The present technology relates to an electric potential measuring device and a method for manufacturing an electric potential measuring device.

BACKGROUND ART

There is an electric potential measuring device in which minute readout electrodes are arranged in an array form and an electric potential generated at the interface between the readout electrode and a solution is electrochemically measured; for example, an electric potential measuring device in which a living cell is put on a readout electrode while the surroundings are filled with a culture fluid and an action potential generated by the living cell is measured is proposed (for example, see Patent Document 1).

In particular, these days, an electric potential measuring device in which electrodes, amplifiers, A/D converters, etc. are integrated on one semiconductor substrate (chip) by using complementary metal-oxide-semiconductor (CMOS) integrated circuit technology and electric potentials are simultaneously measured at multiple points is drawing attention.

CITATION LIST

Patent Document

Patent Document 1: Japanese Patent Application Laid-Open No. 2002-31617

SUMMARY OF THE INVENTION

Problems to be Solved by the Invention

However, the technology proposed by Patent Document 1 has a concern that further improvement in evaluation quality cannot be achieved.

Thus, the present technology has been made in view of such a situation, and a main object of the present technology is to provide an electric potential measuring device that can further improve evaluation quality and a method for manufacturing the electric potential measuring device.

Solutions to Problems

The present inventors conducted extensive studies in order to solve the object described above, and have consequently succeeded in dramatically improving image quality and have completed the present technology.

That is, the present technology firstly provides an electric potential measuring device including:

a plurality of readout electrodes arranged in an array form and each configured to detect an electric potential of an action potential generation point generated by an action of a cell;

an insulating member;

a reference electrode configured to detect a reference potential; and an amplification section configured to obtain a potential difference between a detected electric potential based on the readout electrode and a detected electric potential based on the reference electrode, in which the readout electrode has a covered region where the insulating member is stacked on the readout electrode and an opened region where the insulating member is not stacked on the readout electrode, and the readout electrode has, in the opened region, at least one high portion with high height and/or at least one low portion with low height, with a stacking surface of the readout electrode with the insulating member as a standard.

In the electric potential measuring device according to the present technology, an uneven shape may be formed on a surface of the opened region.

Further, the present technology provides an electric potential measuring device including a plurality of readout electrodes that is arranged in an array form and each of which detects the electric potential of an action potential generation point generated by an action of a cell, an insulating member, a metal member, a reference electrode that detects a reference potential, and an amplification section that obtains the potential difference between a detected electric potential based on the readout electrode and a detected electric potential based on the reference electrode, in which the readout electrode has a covered region where the metal member and the insulating member are stacked in this order on the readout electrode and an opened region where the metal member and the insulating member are not stacked on the readout electrode, and the readout electrode has, in the opened region, at least one high portion with high height and/or at least one low portion with low height, with the stacking surface of the readout electrode with the metal member as a standard.

In the electric potential measuring device according to the present technology, the readout electrode may have, in the opened region, at least one high portion with high height with the stacking surface of the metal member with the insulating member as a standard, and furthermore an uneven shape may be formed on a surface of the opened region.

Furthermore, the present technology provides a method for manufacturing an electric potential measuring device, the method including stacking an insulating member on a readout electrode, forming, on the readout electrode, an opened region where the insulating member is not stacked, and performing an electrochemical oxidation-reduction cycle on the readout electrode having the opened region.

The method for manufacturing an electric potential measuring device according to the present technology may include removing a substance attached to a surface of the opened region, may include forming, on a surface of the opened region, at least one high portion with high height and/or at least one low portion with low height, with the stacking surface of the readout electrode with the insulating member as a standard, and furthermore may include forming an uneven shape on a surface of the opened region.

Furthermore, the present technology provides a method for manufacturing an electric potential measuring device, the method including stacking a metal member and an insulating member in this order on a readout electrode, forming, on the readout electrode, an opened region where the metal member and the insulating member are not stacked, and performing an electrochemical oxidation-reduction cycle on the readout electrode having the opened region.

The method for manufacturing an electric potential measuring device according to the present technology may include removing a substance attached to a surface of the opened region, may include forming, on a surface of the opened region, at least one high portion with high height and/or at least one low portion with low height, with the stacking surface of the readout electrode with the metal member as a standard, may include forming, on a surface of the opened region, at least one high portion with high height with the stacking surface of the metal member with the insulating member as a standard, and furthermore may include forming an uneven shape on a surface of the opened region.

Effects of the Invention

According to the present technology, evaluation quality can be further improved. Note that the effect described herein is not necessarily a limitative one, and any of the effects described in the present disclosure is possible.

BRIEF DESCRIPTION OF DRAWINGS

FIGS. 8A, 8B, 8C, and 8D are top views and cross-sectional views showing an example of the method for manufacturing an electric potential measuring device of the third embodiment to which the present technology is applied.

FIGS. 10A, 10B, 10C, and 10D are top views and cross-sectional views showing an example of the method for manufacturing an electric potential measuring device of the fourth embodiment to which the present technology is applied.

MODE FOR CARRYING OUT THE INVENTION

Figure 1:
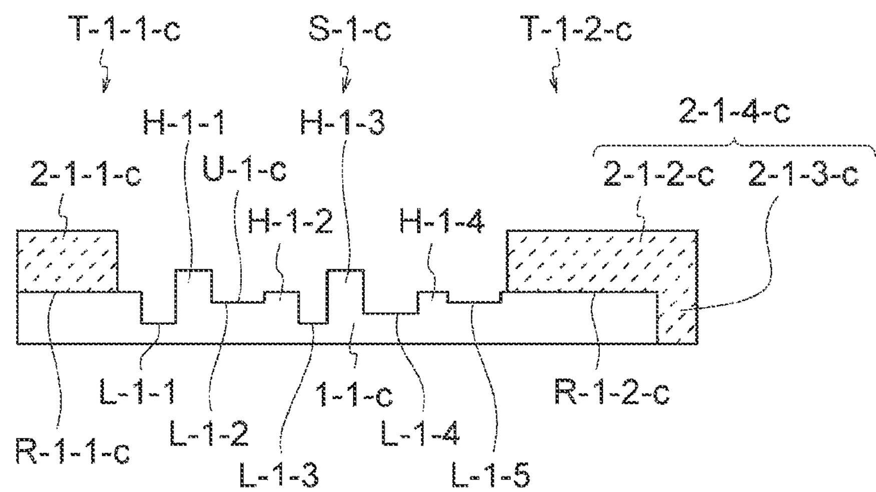
FIG. 1 is a cross-sectional view showing a configuration example of a readout electrode included in an electric potential measuring device of a first embodiment to which the present technology is applied.

Hereinbelow, preferred forms for implementing the present technology are described. The embodiments described below show examples of representative embodiments of the present technology, and the scope of the present technology should not be construed as being limited by these. Note that, unless otherwise specified, in the description of a drawing, a term including "upper" means the upward direction, the upper side, or an upper portion in the drawing, a term including "lower" means the downward direction, the lower side, or a lower portion in the drawing, a term including "left" means the left direction, the left side, or a left portion in the drawing, and a term including "right" means the right direction, the right side, or a right portion in the drawing.

Note that the description is given in the following order.

1. Outline of present technology
2. First embodiment (example 1 of electric potential measuring device)
3. Second embodiment (example 2 of electric potential measuring device)
4. Third embodiment (example 1 of method for manufacturing electric potential measuring device)
5. Fourth embodiment (example 2 of method for manufacturing electric potential measuring device)

1. Outline of Present Technology

First, an outline of the present technology is described.

There is a technology in which, for example, platinum fine particles are accumulated on a surface of an electrode by electroplating to increase the surface area. However, to perform the plating of platinum, it is necessary to use a highly toxic chemical substance such as chloroplatinic acid or an ammonia solution of platinum nitrite; in a case where chloroplatinic acid or an ammonia solution of platinum nitrite remains on a surface of an electrode array or a package member, cell culture or the acquisition and evaluation of an action potential subsequently performed is influenced. Further, in a case where platinum is deposited on a surface of an electrode, also the risk of a short circuit between electrodes occurs. Furthermore, even in a case where the effective surface area is increased in this way, in a case where the surface of the electrode is exposed to the environment, the attachment of impurities of the surrounding atmosphere progresses on the surface of the platinum electrode, which is rich in reactivity, and soon the effective surface area decreases.

The present technology has been made in view of the circumstances mentioned above. An object of the present technology is to provide an electric potential measuring device that can further improve evaluation quality and a method for manufacturing the electric potential measuring device; in particular, an object of the present technology is to provide an electric potential measuring device that can two-dimensionally measure a feeble cell action potential, with high resolution and low noise, and a method for manufacturing the electric potential measuring device.

In a case where the propagation or the like of an action potential between cells is performed two-dimensionally with high resolving power, it is necessary that the pitch of electrodes disposed in an array form be reduced up to not more than a dimension corresponding to the size of the cell. As a result, the surface area of the electrode is inevitably reduced, an increase in the impedance of the electrode interface occurs, and an increase in background noise derived from the impedance increase occurs. To suppress this, it is necessary that the surface area of the electrode be increased by some kind of method. In particular, in a case where an evaluation of propagation between cells of which the action potential serving as a signal is small (for example, nerve cells or the like) is performed, if the reduction of noise is not performed, distinction with the action potential is difficult. Thus, an improvement in evaluation quality by the present technology proposed by the present application is necessary.

Next, a relationship between noise and impedance is described. As shown by Formula (1) below, there is a formula showing a relationship between noise and impedance.

[Math. 1]

$$\overline{v_{n,in}^2}(\text{Observed noise}) \approx 4kTR_s \cdot \Delta f + \frac{kT}{C_{es,s}} \qquad \text{Formula (1)}$$

In Formula (1), k represents the Boltzmann constant, T represents the absolute temperature, and $C_{es,s}$ represents the electrode capacitance. From Formula (1), it can be understood that the value of the observed noise is in inverse proportion to the value of the electrode capacitance ($C_{es,s}$). That is, if the electrode capacitance increases, the observed noise decreases.

The present technology can make the expansion of the effective surface area by the removal of impurities of the surface of the electrode and the formation of unevenness. Thereby, the electrode impedance can be lowered, the suppression of electrode noise can be made, the S/N ratio is improved, and a minute signal can be acquired with a minute electrode array. The present technology can make the expansion of the surface area of a readout electrode in a simple manner immediately before the shipment of the device (the electric potential measuring device) or immediately before the user's using, for example, and is effective for improvement in evaluation quality.

In the following, the present technology is described in detail.

2. First Embodiment (Example 1 of Electric Potential Measuring Device)

An electric potential measuring device of a first embodiment according to the present technology (example 1 of the electric potential measuring device) is an electric potential measuring device including a plurality of readout electrodes that is arranged in an array form and each of which detects the electric potential of an action potential generation point generated by an action of a cell, an insulating member, a reference electrode that detects a reference potential, and an amplification section that obtains the potential difference between a detected electric potential based on the readout electrode and a detected electric potential based on the reference electrode, in which the readout electrode has a covered region where the insulating member is stacked on the readout electrode and an opened region where the insulating member is not stacked on the readout electrode, and the readout electrode has, in the opened region, at least one high portion with high height and/or at least one low portion with low height, with the stacking surface of the readout electrode with the insulating member as a standard.

In the electric potential measuring device according to the first embodiment of the present technology, an uneven shape may be formed on a surface of the opened region.

The electric potential measuring device of the first embodiment according to the present technology has, in the opened region possessed by the readout electrode, at least one high portion with high height and/or at least one low portion with low height (for example, an uneven shape), with the stacking surface of the readout electrode with the insulating member as a standard, and can thereby make the expansion of the effective surface area of the opened region (the readout electrode). Therefore, by the electric potential measuring device of the first embodiment according to the present technology, the electrode impedance can be lowered, the suppression of electrode noise can be made, further the S/N ratio is improved, and a minute signal can be acquired with a minute electrode array. The electric potential measuring device of the first embodiment according to the present technology can two-dimensionally measure a feeble cell action potential, with high resolution and low noise.

In addition, the electric potential measuring device of the first embodiment according to the present technology can make further expansion of the effective surface area of the opened region (the readout electrode) by removing impurities of the surface of the readout electrode in the opened region. Therefore, by the electric potential measuring device of the first embodiment according to the present technology, the electrode impedance can be further lowered, further suppression of electrode noise can be made, further the S/N ratio is further improved, and a minute signal can be acquired with a minute electrode array. As the impurities on the surface of the electrode, substances that are generated during the manufacturing course such as the processing and formation of the electric potential measuring device and are adsorbed on the surface of the electrode, contaminants that are floating in the air after the completion of the electric potential measuring device and are attached to the surface of the electrode, and the like are given.

A readout electrode included in an electric potential measuring device of the first embodiment according to the present technology will now be described using FIG. 1. FIG. 1 is a cross-sectional view showing a configuration example of a readout electrode included in an electric potential measuring device of the first embodiment according to the present technology (readout electrode 1-1-*c*).

As shown in FIG. 1, in the left side of FIG. 1, insulating member 2-1-*c* is stacked on the upper side of unit electrode (readout electrode) 1-1-*c*, and covered region T-1-1-*c* possessed by unit electrode 1-1-*c* is formed. In the right side of FIG. 1, insulating member 2-1-4-*c* is provided on the upper side of unit electrode 1-1-*c* and on the right side surface. In more detail, insulating member 2-1-2-*c* is stacked on the upper side of unit electrode 1-1-*c* and covered region T-1-2-*c* possessed by unit electrode 1-1-*c* is formed, and the right side surface of unit electrode 1-1-*c* is covered with insulating member 2-1-3-*c* so as to separate the right neighboring unit electrode (not illustrated). In addition, as shown in FIG.

1, opened region S-1-*c* where the insulating member is not stacked on the upper side of unit electrode 1-1-*c* is formed on unit electrode 1-1-*c*.

In addition, as shown in FIG. 1, on the surface of opened region S-1-*c* of unit electrode 1-1-*c* (an action electrode), high portion H-1-1 and high portion H-1-3 with high height with stacking surface R-1-1-*c* of unit electrode 1-1-*c* with insulating member 2-1-1-*c* and stacking surface R-1-2-*c* of unit electrode 1-1-*c* with insulating member 2-1-2-*c* as a standard are formed, and high portion H-1-2 and high portion H-1-4 with substantially equal heights with stacking surface R-1-1-*c* and stacking surface R-1-2-*c* as a standard are formed.

Further, on the surface of opened region S-1-*c* of unit electrode 1-1-*c* (an action electrode), low portion L-1-1, low portion L-1-2, low portion L-1-3, low portion L-1-4, and low portion L-1-5 with low height with stacking surface R-1-1-*c* of unit electrode 1-1-*c* with insulating member 2-1-1-*c* and stacking surface R-1-2-*c* of unit electrode 1-1-*c* with insulating member 2-1-2-*c* as a standard are formed.

The value obtained by adding up the positive volumes of high portions H-1-1 to H-1-4 with stacking surface R-1-1-*c* and stacking surface R-1-2-*c* as a standard (the positive amounts of the electrode material of the unit electrode) and the negative volumes of low portions L-1-1 to L-1-5 with stacking surface R-1-1-*c* and stacking surface R-1-2-*c* as a standard (the negative amounts of the electrode material of the unit electrode) is substantially zero. That is, the volume of unit electrode 1-1-*c* (the amount of the electrode material of the unit electrode) is substantially equal to the volume of a unit electrode that is substantially flat with stacking surface R-1-1-*c* and stacking surface R-1-2-*c* as a standard (the amount of the electrode material of the unit electrode). Further, on unit electrode 1-1-*c*, an uneven shape based on high portions H-1-1 to H-1-4 and low portions L-1-1 to L-1-5 is formed with surface U-1-*c* as a standard.

Thus, the effective surface area of unit electrode 1-1-*c* (an action electrode) on which an uneven shape based on high portions H-1-1 to H-1-4 and low portions L-1-1 to L-1-5 is formed is increased relative to the surface area of a unit electrode that is substantially flat with stacking surface R-1-2-*c* as a standard and to which impurities are attached (for example, unit electrodes 1-1-*a* and 1-1-*b*). By the increase of the surface area, the electrode impedance is lowered, and background noise in a case where electric potential is measured with a minute electrode array can be suppressed.

FIGS. 6A, 6B, 6C, 6D, and 6E are diagrams for describing increases in roughness (for example, an uneven shape, a shape having high portions and low portions, or the like) associated with oxidation-reduction cycles of surfaces of readout electrodes (for example, unit electrode 1-1-*c*, and unit electrode 1-2-*c* described later). The surface of the readout electrode is observed with a scanning tunneling microscope, and FIGS. 6A 6B, 6C, 6D, and 6E are diagrams based on the observation.

Figure 6A:
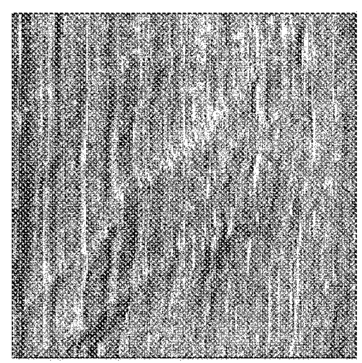
FIGS. 6A, 6B, 6C, 6D, and 6E are diagrams for describing increases in roughness associated with oxidation-reduction cycles of surfaces of readout electrodes.
Figure 6B:
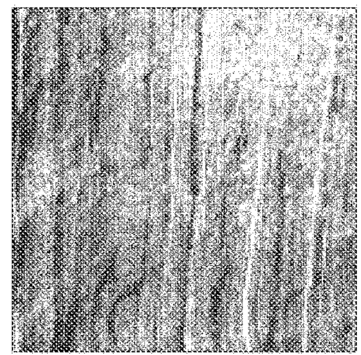
Figure 6C:
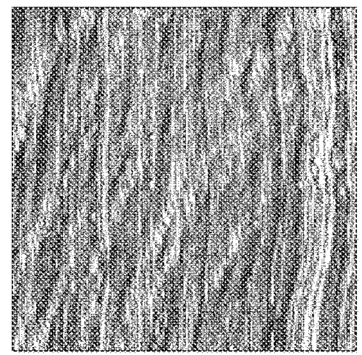
Figure 6D:
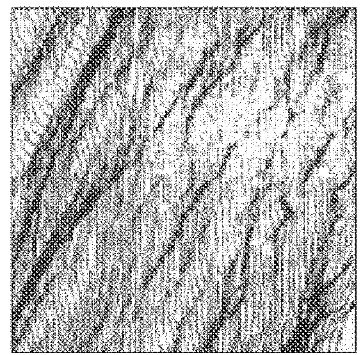
Figure 6E:
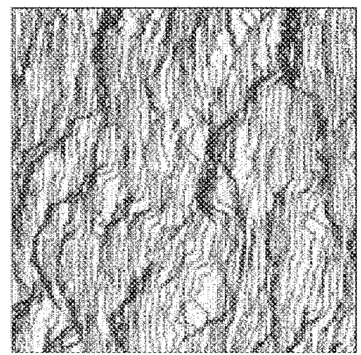

FIG. 6A is a diagram of a surface of a readout electrode after an oxidation-reduction cycle (−0.22↔1.15 V) is repeated 20 times, FIG. 6B is a diagram of a surface of a readout electrode after an oxidation-reduction cycle (−0.22↔1.15 V) is repeated 60 times, and FIG. 6C is a diagram of a surface of a readout electrode after an oxidation-reduction cycle (−0.22↔1.15 V) is repeated 240 times. In addition, FIGS. 6D and 6E are diagrams of a surface of a readout electrode after an oxidation-reduction cycle (−0.22↔1.15 V) is repeated 480 times; FIGS. 6D and 6E are diagrams of the surface of the readout electrode in different observation places (two visual fields). As is clear from FIGS. 6A, 6B, 6C, 6D, and 6E, it can be seen that, as the number of times of oxidation-reduction cycles increases, the roughness (for example, an uneven shape, a shape having high portions and low portions, or the like) of the surface of the readout electrode increases.

Figure 3:
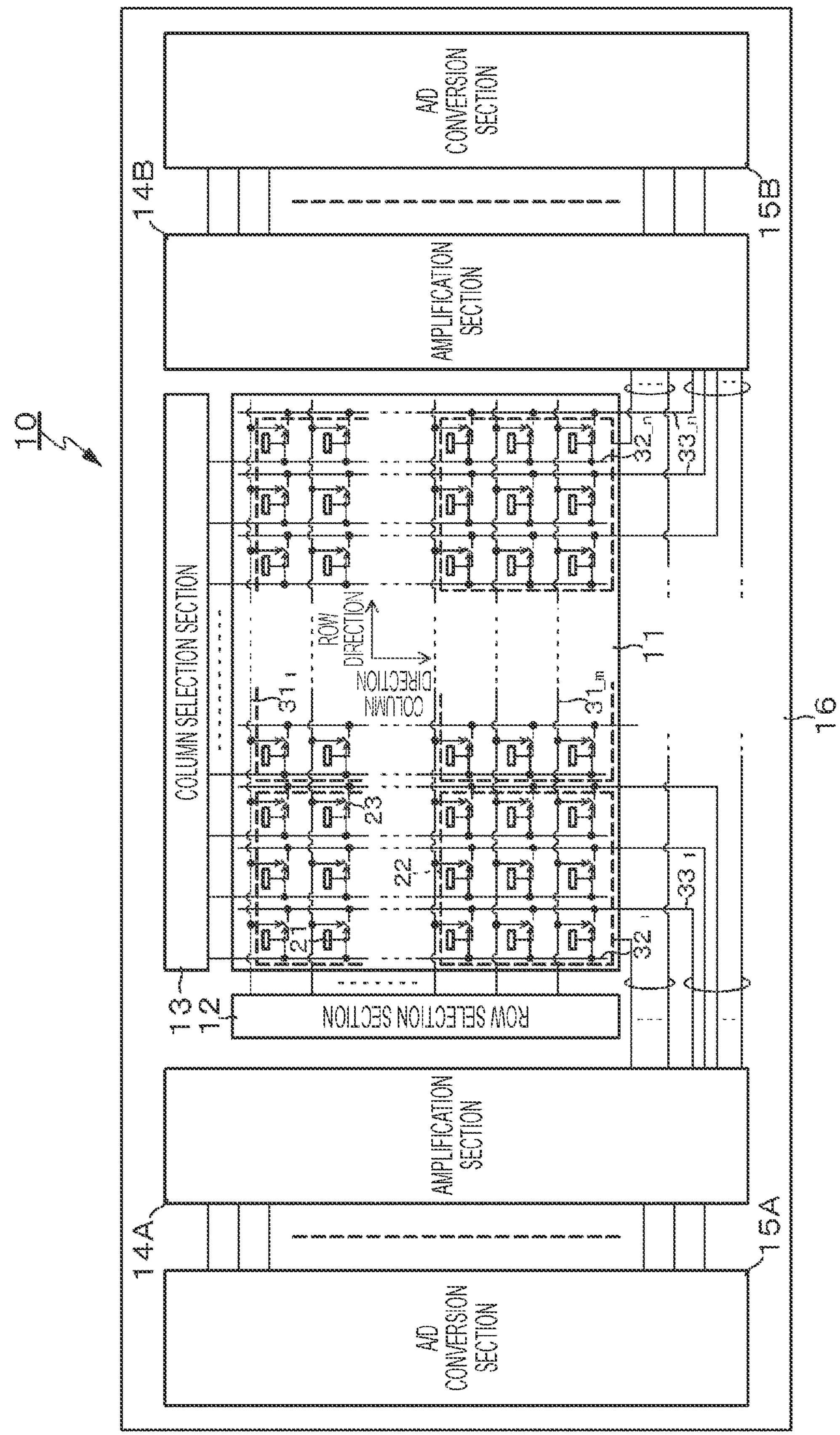
FIG. 3 is a configurational diagram showing an overview of a configuration of the electric potential measuring device of the first embodiment or the second embodiment to which the present technology is applied.
Figure 4:
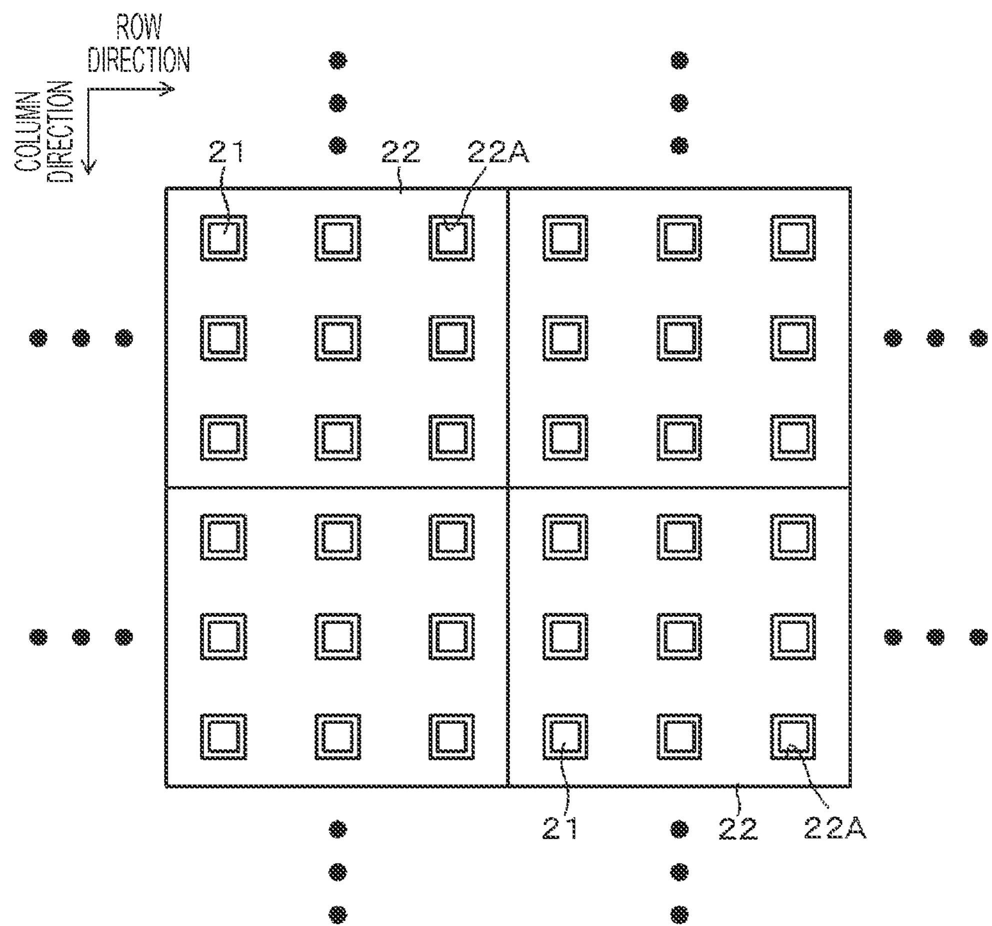
FIG. 4 is a plan view showing an example of an electrode arrangement of reference electrodes each having a square electrode shape and readout electrodes.
Figure 5:
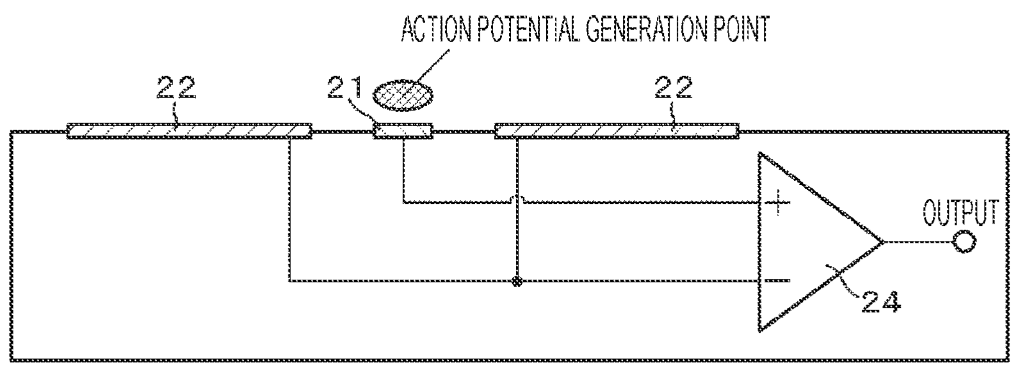
FIG. 5 is a schematic diagram showing an example of a wiring structure between a readout electrode and a reference electrode, and a differential amplifier.

Next, an electric potential measuring device of the first embodiment according to the present technology is described using FIG. 3 to FIG. 5.

FIG. 3 is a configurational diagram showing an overview of a configuration of an electric potential measuring device of the first embodiment according to the present technology. An electric potential measuring device 10 of the first embodiment according to the present technology is a device in which an electrode section 11, a row selection section 12, a column selection section 13, amplification sections 14A and 14B, and A/D conversion sections 15A and 15B that are created by using CMOS integrated circuit technology are integrated on one semiconductor substrate (semiconductor chip) 16. Herein, a configuration in which amplification sections 14A and 14B and A/D conversion sections 15A and 15B are arranged on both sides across the electrode section 11 is employed; however, it is also possible to employ a configuration in which they are arranged on one side of the electrode section 11.

In the electrode section 11, a plurality of readout electrodes 21 each of which detects the electric potential of an action potential generation point generated by an action of a cell is arranged in an array form of m rows by n columns. The readout electrode 21 has, for example, an electrode size approximately equal to the size of the action potential generation point. Reference electrodes 22 each of which detects a reference potential are arranged in the array of the readout electrodes 21. The readout electrode 21 is, for example, unit electrode 1-1-*c* described in FIG. 1 above. In addition, as described in FIG. 1, an insulating member may be stacked on the readout electrode 21.

Herein, as an example, reference electrodes 22 are arranged in units of three readout electrodes 21 in each of the row direction and the column direction, i.e., a total of nine readout electrodes 21; the electrode size of the readout electrode 21 is smaller than the electrode size of the reference electrode 22. In other words, the electrode size of the reference electrode 22 is larger than the electrode size of the readout electrode 21. The reference potential that the reference electrode 22 detects is a standard potential serving as a standard at the time of taking the difference with the electric potential of the action potential generation point that the readout electrode 21 detects. The electrode structures of the readout electrode 21 and the reference electrode 22 are planar structures.

For the arrangement of the readout electrodes 21 of m rows by n columns, row selection lines $\mathbf{31}_{\_1}$ to $\mathbf{31}_{\_m}$ are drawn on a row basis, and column selection lines $\mathbf{32}_{\_1}$ to $\mathbf{32}_{\_n}$ and signal readout lines $\mathbf{33}_{\_1}$ to $\mathbf{33}_{\_n}$ are drawn on a column basis. Each of one ends of row selection lines $\mathbf{31}_{\_1}$ to $\mathbf{31}_{\_m}$ is connected to an output terminal of the corresponding row of the row selection section 12. Each of one ends of column selection lines $\mathbf{32}_{\_1}$ to $\mathbf{32}_{\_n}$ is connected to an output terminal of the corresponding column of the column selection section 13.

The readout electrode 21 is connected to any of signal readout lines $\mathbf{33}_{\_1}$ to $\mathbf{33}_{\_n}$ via a switch 23. In FIG. 3, the switch 23 is shown as one switch for simplification of the drawing; however, in practice, the switch 23 includes at least two switches for row selection and for column selection.

Further, in correspondence with this, also each of signal readout lines 33$_{\_1}$ to 33$_{\_n}$ includes at least two signal readout lines.

In the switch 23, for example, the switch for row selection is driven to ON (closed) by a row selection signal applied from the row selection section 12 via any of row selection lines 31$_{\_1}$ to 31$_{\_m}$, and the switch for column selection is driven to ON by a column selection signal applied from the column selection section 13 via any of column selection lines 32$_{\_1}$ to 32$_{\_n}$. By these switches for row selection and for column selection becoming ON, an electric potential detected by the readout electrode 21 is output to any of signal readout lines 33$_{\_1}$ to 33$_{\_n}$, and is transmitted to amplification section 14A or 14B by the same one of signal readout lines 33$_{\_1}$ to 33$_{\_n}$.

Note that, although herein a description is given by taking mainly the electric potential readout system of the readout electrode 21, also the electric potential readout system of the reference electrode 22 basically has a similar configuration. Specifically, two electric potential readout systems each including the row selection section 12, the column selection section 13, row selection lines 31$_{\_1}$ to 31$_{\_m}$, column selection lines 32$_{\_1}$ to 32$_{\_n}$, and signal readout lines 33$_{\_1}$ to 33$_{\_n}$ are provided for the electric potential readout of the readout electrode 21 and for the electric potential readout of the reference electrode 22.

The detected electric potential of the readout electrode 21 and the detected electric potential of the reference electrode 22 read out by the two electric potential readout systems are supplied to amplification section 14A or 14B. Each of amplification sections 14A and 14B includes a plurality of differential amplifiers provided in common to a plurality of readout electrodes 21, and takes the difference between the detected electric potential of the reference electrode 22 (the reference potential) and the detected electric potential of each of the nine readout electrodes 21 belonging to the same reference electrode 22, in units of, for example, reference electrodes 22. This difference is supplied to A/D conversion section 15A or 15B. Each of A/D conversion sections 15A and 15B A/D-converts the difference output from amplification section 14A or 14B, and outputs the result as a digital value corresponding to the electric potential detected by the readout electrode 21.

In the electric potential measuring device 10 of the configuration mentioned above, the reference electrode 22 is placed in the vicinity of the readout electrode 21, specifically in the array of readout electrodes 21. In addition, the size of the reference electrode 22 is larger than the size of the readout electrode 21. Electrodes of various shapes may be used as the reference electrode 22. An example in which the electrode shape of the reference electrode 22 is a square is shown in FIG. 4.

FIG. 4 shows an example in which, on the basis of the relationship corresponding to FIG. 3, reference electrode 22 is arranged in units of three readout electrodes 21 in each of the row direction and the column direction, i.e., a total of nine readout electrodes 21. One reference electrode 22 has, in its plane, nine openings 22A in positions corresponding to nine readout electrodes 21 of a matrix-form arrangement. In addition, the reference electrodes 22 are arranged such that nine readout electrodes 21 of a matrix-form arrangement are located individually in the nine openings 22A. In other words, the readout electrode 21 is placed so as to be located in the opening 22A of the reference electrode 22.

An electrode arrangement of readout electrodes 21 and reference electrodes 22 like that shown in FIG. 4 is suitable to read out a local potential change. As an example, to read out an action potential of a living cell with a size of approximately 5 [μm], readout electrodes 21 each with an electrode size of approximately 5 [μm] and reference electrodes 22 each with a size of not less than 10 times of this, that is, a size of not less than 50 [μm] are arranged.

In such a case, a portion where an action potential is generated is equivalent to one local point. There is an approximately tenfold difference in potential fluctuation between a readout electrode 21 with a size of 5 [μm] and a reference electrode 22 with a size of 50 [μm], that is, the potential fluctuation is about 10 times. Then, the difference between the electric potential detected by the readout electrode 21 and the electric potential detected by the reference electrode 22 is taken; thus, the action potential of the living cell can be measured.

FIG. 5 shows an example of wiring between the readout electrode 21 and the reference electrode 22, and one differential amplifier of amplification section 14A or 14B. The position of the readout electrode 21 and the position of the reference electrode 22 can be equalized to the position of a differential amplifier 24 by employing a configuration in which, as described above, the reference electrode 22 is placed in the vicinity of the readout electrode 21, more specifically in the array of readout electrodes 21. Thus, the wiring capacity and the capacity with the environment are almost electrically equal between two wires that connect the readout electrode 21 and the reference electrode 22, and two input terminals of the differential amplifier 24, and noises superimposed on these wires can be equalized; therefore, noise included in the output of the differential amplifier 24 when the difference is taken can be suppressed.

3. Second Embodiment (Example 2 of Electric Potential Measuring Device)

An electric potential measuring device according to a second embodiment of the present technology (example 2 of an electric potential measuring device) includes a plurality of readout electrodes that is arranged in an array form and each of which detects the electric potential of an action potential generation point generated by an action of a cell, an insulating member, a metal member, a reference electrode that detects a reference potential, and an amplification section that obtains the potential difference between a detected electric potential based on the readout electrode and a detected electric potential based on the reference electrode, in which the readout electrode has a covered region where the metal member and the insulating member are stacked in this order on the readout electrode and an opened region where the metal member and the insulating member are not stacked on the readout electrode, and the readout electrode has, in the opened region, at least one high portion with high height and/or at least one low portion with low height, with the stacking surface of the readout electrode with the metal member as a standard.

In the electric potential measuring device according to the second embodiment of the present technology, the readout electrode may have, in the opened region, at least one high portion with high height with the stacking surface of the metal member with the insulating member as a standard. Further, in the electric potential measuring device according to the second embodiment of the present technology, an uneven shape may be formed on a surface of the opened region.

The electric potential measuring device of the second embodiment according to the present technology has, in the opened region, at least one high portion with high height and/or at least one low portion with low height (for example, an uneven shape), with the stacking surface of the readout electrode with the metal member as a standard, and can thereby make the expansion of the effective surface area of the opened region (the readout electrode). Therefore, by the electric potential measuring device of the second embodiment according to the present technology, the electrode impedance can be lowered, the suppression of electrode noise can be made, further the S/N ratio is improved, and a minute signal can be acquired with a minute electrode array. The electric potential measuring device of the second embodiment according to the present technology can two-dimensionally measure a feeble cell action potential, with high resolution and low noise.

In addition, the electric potential measuring device of the second embodiment according to the present technology can make further expansion of the effective surface area of the opened region (the readout electrode) by removing impurities of the surface of the readout electrode in the opened region. Therefore, by the electric potential measuring device of the second embodiment according to the present technology, the electrode impedance can be further lowered, further suppression of electrode noise can be made, further the S/N ratio is further improved, and a minute signal can be acquired with a minute electrode array. As the impurities on the surface of the electrode, substances that are generated during the manufacturing course such as the processing and formation of the electric potential measuring device and are adsorbed on the surface of the electrode, contaminants that are floating in the air after the completion of the electric potential measuring device and are attached to the surface of the electrode, and the like are given.

Figure 2:
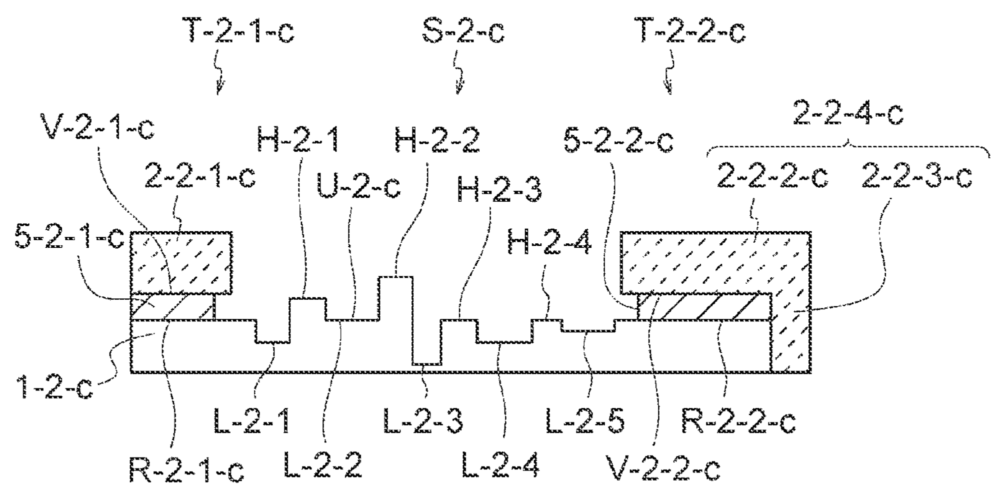
FIG. 2 is a cross-sectional view showing a configuration example of a readout electrode included in an electric potential measuring device of a second embodiment to which the present technology is applied.

A readout electrode included in an electric potential measuring device of the second embodiment according to the present technology will now be described using FIG. 2. FIG. 2 is a cross-sectional view showing a configuration example of a readout electrode included in an electric potential measuring device of the second embodiment according to the present technology.

As shown in FIG. 2, in the left side of FIG. 2, metal member 5-2-1-*c* and insulating member 2-2-1-*c* are stacked in this order on the upper side of unit electrode 1-2-*c*, and covered region T-2-1-*c* of unit electrode 1-2-*c* is formed. In the right side of FIG. 2, insulating member 2-2-4-*c* is provided on the upper side of metal member 5-2-2-*c* stacked on the upper side of unit electrode 1-2-*c* and on the right side surfaces of unit electrode 1-2-*c* and metal member 5-2-2-*c*. In more detail, metal member 5-2-2-*c* and insulating member 2-2-2-*c* are stacked in this order on the upper side of unit electrode 1-2-*c* and covered region T-2-2-*c* of unit electrode 1-2-*c* is formed, and the right side surfaces of unit electrode 1-2-*c* and metal member 5-2-2-*c* are covered with insulating member 2-2-3-*c* so as to separate the right neighboring unit electrode (not illustrated) and the metal member. In addition, as shown in FIG. 2, on unit electrode 1-2-*c*, the metal member corresponding to the place not covered with insulating member 2-2-1-*c* or 2-2-2-*c* in the above manner is melted, and opened region S-2-*c* where the insulating member and the metal member are not stacked on the upper side of unit electrode 1-2-*c* is formed.

In addition, the surface of unit electrode 1-2-*c* (an action electrode) is oxidized and reduced by the processing of electrochemical oxidation-reduction cycles; thus, on the surface of opened region S-2-*c* of unit electrode 1-2-*c* (an action electrode), high portion H-2-1 and high portion H-2-2 with high height with stacking surface R-2-1-*c* of unit electrode 1-2-*c* with metal member 5-2-1-*c* and stacking surface R-2-2-*c* of unit electrode 1-1-*c* with metal member 5-2-2-*c* as a standard are formed, and high portion H-2-3 and high portion H-2-4 with substantially equal heights with stacking surface R-2-1-*c* and stacking surface R-2-2-*c* as a standard are formed. High portion H-2-2 is high also with the stacking surface V-2-1-*c* of unit electrode 1-2-*c* with insulating member 2-2-1-*c* and the stacking surface V-2-2-*c* of unit electrode 1-1-*c* with insulating member 2-2-2-*c* as a standard.

Further, on the surface of opened region S-1-*c* of unit electrode 1-2-*c* (an action electrode), low portion L-2-1, low portion L-2-2, low portion L-2-3, low portion L-2-4, and low portion L-2-5 with low height with stacking surface R-2-1-*c* of unit electrode 1-2-*c* with metal member 5-2-1-*c* and stacking surface R-2-2-*c* of unit electrode 1-1-*c* with metal member 5-2-2-*c* as a standard are formed.

The value obtained by adding up the positive volumes of high portions H-2-1 to H-2-4 with stacking surface R-2-1-*c* and stacking surface R-2-2-*c* as a standard (the positive amounts of the electrode material of the unit electrode) and the negative volumes of low portions L-2-1 to L-2-5 with stacking surface R-2-1-*c* and stacking surface R-2-2-*c* as a standard (the negative amounts of the electrode material of the unit electrode) is substantially zero. That is, the volume of unit electrode 1-2-*c* (the amount of the electrode material of the unit electrode) is substantially equal to the volume of a unit electrode that is substantially flat with stacking surface R-2-1-*c* and stacking surface R-2-2-*c* as a standard (for example, unit electrodes 1-2-*a* and 1-2-*b*) (the amount of the electrode material of the unit electrode). Further, on unit electrode 1-1-*c*, an uneven shape based on high portions H-1-1 to H-1-4 and low portions L-1-1 to L-1-5 is formed with surface U-1-*c* as a standard.

Thus, the effective surface area of unit electrode 1-2-*c* (an action electrode) on which an uneven shape based on high portions H-2-1 to H-2-4 and low portions L-2-1 to L-2-5 is formed is increased relative to the surface area of a unit electrode that is substantially flat with stacking surface R-2-1-*c* and stacking surface R-2-2-*c* as a standard and to which impurities are attached (for example, unit electrodes 1-2-*a* and 1-2-*b*). By the increase of the surface area, the electrode impedance is lowered, and background noise in a case where electric potential is measured with a minute electrode array can be suppressed.

The subject matter of FIGS. 3, 4, 5, 6A, 6B, 6C, 6D, and 6E described in the above can be applied as it is to the electric potential measuring device of the second embodiment according to the present technology. In addition, the readout electrode 21 is, for example, unit electrode 1-2-*c* described in FIG. 2 above. In addition, as described in FIG. 2, a metal member and an insulating member may be stacked in this order on the readout electrode 21.

4. Third Embodiment (Example 1 of Method for Manufacturing Electric Potential Measuring Device)

A method for manufacturing an electric potential measuring device of a third embodiment according to the present technology (example 1 of a method for manufacturing an electric potential measuring device) is a manufacturing method including stacking an insulating member on a readout electrode, forming, on the readout electrode, an opened region where the insulating member is not stacked, and performing an electrochemical oxidation-reduction cycle on the readout electrode having the opened region. Further, modification examples of the method for manufacturing an electric potential measuring device of the third embodiment according to the present technology (example 1 of the method for manufacturing an electric potential measuring device) include a method for manufacturing an electric potential measuring device including performing an electrochemical oxidation-reduction cycle on a readout electrode, a method for manufacturing an electric potential measuring device including performing an electrochemical oxidation-reduction cycle on a readout electrode and removing a substance attached to a surface of the readout electrode, and a method for manufacturing an electric potential measuring device including performing an electrochemical oxidation-reduction cycle on a readout electrode, removing a substance attached to a surface of the readout electrode, and forming an uneven shape on the surface of the readout electrode. The electric potential measuring device manufactured by using the method for manufacturing an electric potential measuring device of the third embodiment according to the present technology can two-dimensionally measure a feeble cell action potential, with high resolution and low noise. Further, the electric potential measuring device manufactured by using any of the modification examples of the method for manufacturing an electric potential measuring device of the third embodiment according to the present technology can two-dimensionally measure a feeble cell action potential, with high resolution and low noise.

The method for manufacturing an electric potential measuring device according to the third embodiment of the present technology may include removing a substance attached to a surface of the opened region. In addition, the method for manufacturing an electric potential measuring device according to the third embodiment of the present technology may include forming, on a surface of the opened region, at least one high portion with high height and/or at least one low portion with low height, with the stacking surface of the readout electrode with the insulating member as a standard, may include forming, on a surface of the opened region, an uneven shape on a surface of the opened region.

A method for manufacturing an electric potential measuring device of the third embodiment according to the present technology will now be described using FIGS. 7A, 7B, 7C, 8A, 8B, 8C, and 8D. Note that an electric potential measuring device of the third embodiment according to the present technology can be manufactured by, except for the subject matter described in FIGS. 7A, 7B, 7C, 8A, 8B, 8C, and 8D, using a known method (for example, WO 2017/061171 A1).

Figure 7A:
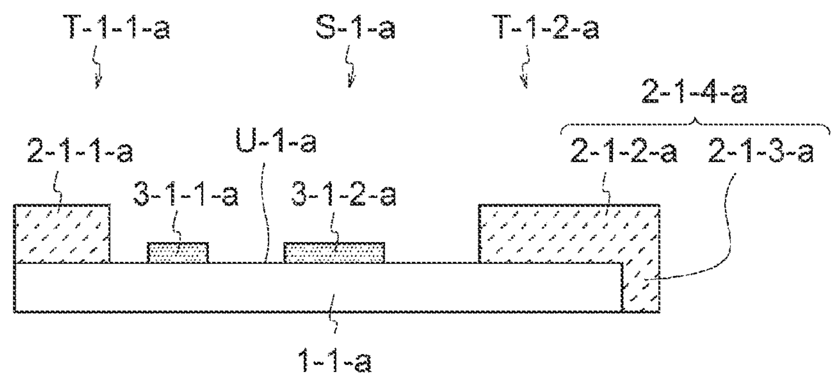
FIGS. 7A, 7B, and 7C are cross-sectional views showing an example of a method for manufacturing an electric potential measuring device of a third embodiment to which the present technology is applied.
Figure 7B:
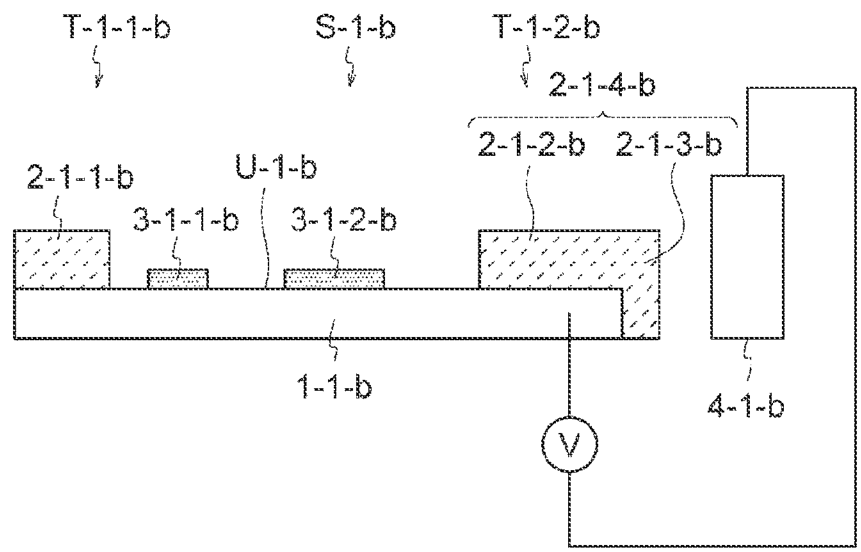
Figure 7C:
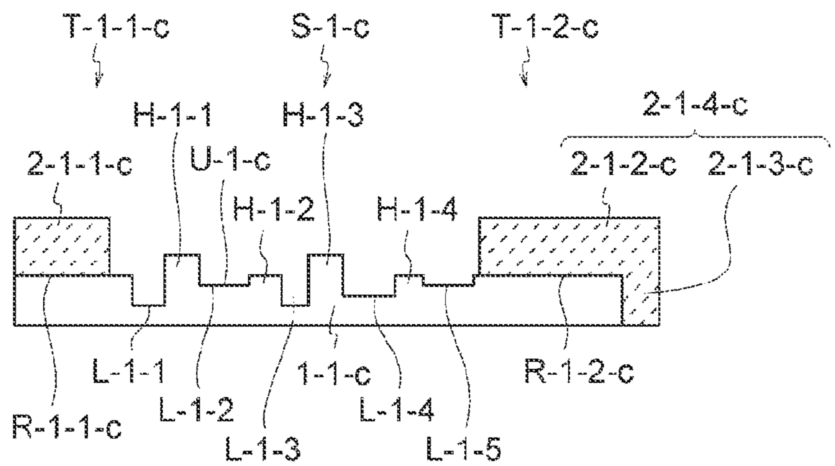

FIGS. 7A, 7B, and 7C are cross-sectional views showing an example of a method for manufacturing an electric potential measuring device according to the third embodiment of the present technology. FIGS. 8A, 8B, 8C, 8D are top views and cross-sectional views showing an example of the method for manufacturing an electric potential measuring device according to the third embodiment of the present technology.

First, a method for manufacturing an electric potential measuring device of the third embodiment according to the present technology is described using FIGS. 7A, 7B, and 7C. FIG. 7A shows unit electrode 1-1-*a* of a device (an electric potential measuring device) after a wafer process is ended and then an assembly step is completed. Unit electrode 1-1-*a* (unit electrodes 1-1-*b* and 1-1-*c* in FIGS. 7B and 7C) is an action electrode, and may contain a noble metal electrode material. Examples of the noble metal electrode material include platinum, gold, iridium, rhodium, palladium, and the like. That is, it is sufficient that unit electrode 1-1-*a* be, for example, a platinum electrode or the like.

As shown in FIG. 7A, impurities 3-1-1-*a* and 3-1-2-*a* that have adhered from the environment are attached to surface U-1-*a* of unit electrode 1-1-*a*. In the left side of FIG. 7A, insulating member 2-1-1-*a* is stacked on the upper side of unit electrode 1-1-*a*, and covered region T-1-1-*a* of unit electrode 1-1-*a* is formed. In the right side of FIG. 7A, insulating member 2-1-4-*a* is provided on the upper side of unit electrode 1-1-*a* and on the right side surface of unit electrode 1-1-*a*. In more detail, insulating member 2-1-2-*a* is stacked on the upper side of unit electrode 1-1-*a* and covered region T-1-2-*a* of unit electrode 1-1-*a* is formed, and the right side surface of unit electrode 1-1-*a* is covered with insulating member 2-1-3-*a* so as to separate the right neighboring unit electrode (not illustrated). In addition, as shown in FIG. 7A, opened region S-1-*a* where the insulating member is not stacked on the upper side of unit electrode 1-1-*a* is formed on unit electrode 1-1-*a*.

FIG. 7B is a diagram showing applying a potential difference between unit electrode (action electrode) 1-1-*b* and counter electrode 4-1-*b* in an electrolyte solution (for example, a physiological saline solution) to perform electrochemical oxidation-reduction cycles. For example, as shown in FIG. 7B, the electric potential of unit electrode (action electrode) 1-1-*b* is swept between 0 [V] and 3 [V] 20 times, with counter electrode 4-1-*b* as a standard. Counter electrode 4-1-*b* may be provided on a device of a minute electrode array, or separately a platinum electrode may be prepared and be used while being immersed in an electrolyte solution. As shown in FIG. 7B, impurities 3-1-1-*b* and 3-1-2-*b* that have adhered from the environment are attached to surface U-1-*b* of unit electrode 1-1-*b*. In the left side of FIG. 7B, insulating member 2-1-*b* is stacked on the upper side of unit electrode 1-1-*b*, and covered region T-1-1-*b* of unit electrode 1-1-*b* is formed. In the right side of FIG. 7B, insulating member 2-1-4-*b* is provided on the upper side of unit electrode 1-1-*b* and on the right side surface. In more detail, insulating member 2-1-2-*b* is stacked on the upper side of unit electrode 1-1-*b* and covered region T-1-2-*b* of unit electrode 1-1-*b* is formed, and the right side surface of unit electrode 1-1-*b* is covered with insulating member 2-1-3-*b* so as to separate the right neighboring unit electrode (not illustrated). In addition, as shown in FIG. 7B, opened region S-1-*b* where the insulating member is not stacked on the upper side of unit electrode 1-1-*b* is formed on unit electrode 1-1-*b*.

FIG. 7C shows a manufactured unit electrode (readout electrode) 1-1-*c*. As shown in FIG. 7C, impurities 3-1-1-*b* and 3-1-2-*b* are decomposed and ionized by the processing of electrochemical oxidation-reduction cycles described in FIG. 7B, and impurities 3-1-1-*b* and 3-1-2-*b* can be removed. Like in the description in FIG. 1, in the left side of FIG. 7C, insulating member 2-1-1-*c* is stacked on the upper side of unit electrode 1-1-*c*, and covered region T-1-1-*c* possessed by unit electrode 1-1-*c* is formed. In the right side of FIG. 7C, insulating member 2-1-4-*c* is provided on the upper side of unit electrode 1-1-*c* and on the right side surface. In more detail, insulating member 2-1-2-*c* is stacked on the upper side of unit electrode 1-1-*c* and covered region T-1-2-*c* possessed by unit electrode 1-1-*c* is formed, and the right side surface of unit electrode 1-1-*c* is covered with insulating member 2-1-3-*c* so as to separate the right neighboring unit electrode (not illustrated). In addition, as shown in FIG. 7C, opened region S-1-*c* where the insulating member is not stacked on the upper side of unit electrode 1-1-*c* is formed on unit electrode 1-1-*c*.

In addition, the surface of unit electrode 1-1-*c* (an action electrode) is oxidized and reduced by the processing of electrochemical oxidation-reduction cycles; thus, on the surface of opened region S-1-*c* of unit electrode 1-1-*c* (an action electrode), high portion H-1-1 and high portion H-1-3 with high height with stacking surface R-1-1-*c* of unit electrode 1-1-*c* with insulating member 2-1-1-*c* and stacking surface R-1-2-*c* of unit electrode 1-1-*c* with insulating member 2-1-2-*c* as a standard are formed, and high portion H-1-2 and high portion H-1-4 with substantially equal heights with stacking surface R-1-1-*c* and stacking surface R-1-2-*c* as a standard are formed.

Further, on the surface of opened region S-1-*c* of unit electrode 1-1-*c* (an action electrode), low portion L-1-1, low portion L-1-2, low portion L-1-3, low portion L-1-4, and low portion L-1-5 with low height with stacking surface R-1-1-*c* of unit electrode 1-1-*c* with insulating member 2-1-1-*c* and stacking surface R-1-2-*c* of unit electrode 1-1-*c* with insulating member 2-1-2-*c* as a standard are formed.

The value obtained by adding up the positive volumes of high portions H-1-1 to H-1-4 with stacking surface R-1-1-*c* and stacking surface R-1-2-*c* as a standard (the positive amounts of the electrode material of the unit electrode) and the negative volumes of low portions L-1-1 to L-1-5 with stacking surface R-1-1-*c* and stacking surface R-1-2-*c* as a standard (the negative amounts of the electrode material of the unit electrode) is substantially zero. That is, the volume of unit electrode 1-1-*c* (the amount of the electrode material of the unit electrode) is substantially equal to the volume of a unit electrode that is substantially flat with stacking surface R-1-1-*c* and stacking surface R-1-2-*c* as a standard (for example, unit electrodes 1-1-*a* and 1-1-*b*) (the amount of the electrode material of the unit electrode). Further, on unit electrode 1-1-*c*, an uneven shape based on high portions H-1-1 to H-1-4 and low portions L-1-1 to L-1-5 is formed with surface U-1-*c* as a standard.

Thus, by removing impurities, the effective surface area of unit electrode 1-1-*c* (an action electrode) on which an uneven shape based on high portions H-1-1 to H-1-4 and low portions L-1-1 to L-1-5 is formed is increased relative to the surface area of a unit electrode that is substantially flat with stacking surface R-1-1-*c* and stacking surface R-1-2-*c* as a standard and to which impurities are attached (for example, unit electrodes 1-1-*a* and 1-1-*b*). By the increase of the surface area, the electrode impedance is lowered, and background noise in a case where electric potential is measured with a minute electrode array can be suppressed. The electric potential measuring device manufactured by using unit electrode 1-1-*c* can two-dimensionally measure a feeble cell action potential, with high resolution and low noise.

Next, the method for manufacturing an electric potential measuring device of the third embodiment according to the present technology is described using FIGS. 8A, 8B, 8C, and 8D. FIG. 8A is a top view of unit electrode 1-3-*a* of a device (an electric potential measuring device) after a wafer process is ended and then an assembly step is completed. Unit electrode 1-3-*a* (unit electrodes 1-3-*b* to 1-3-*d* in FIGS. 8B, 8C, and 8D) is an action electrode, and may contain a noble metal electrode material. Examples of the noble metal electrode material include platinum, gold, iridium, rhodium, palladium, and the like. That is, it is sufficient that unit electrode 1-3-*a* be, for example, a platinum electrode or the like.

As shown in FIG. 8A, for example, impurities 3-3-1-*a* and 3-3-2-*a* that have adhered from the environment are attached to unit electrode 1-3-*a*. As shown in FIG. 8A, insulating member 2-3-*a* is provided on the outer circumference of unit electrode 1-3-*a*.

FIG. 8B is a top view of a manufactured unit electrode (readout electrode) 1-3-*b*. As shown in FIG. 8B, impurities 3-3-1-*a* and 3-3-2-*a* are decomposed and ionized by the processing of electrochemical oxidation-reduction cycles and impurities 3-3-1-*a* and 3-3-2-*a* are removed, and an uneven shape based on high portions and low portions is formed on unit electrode (readout electrode) 1-3-*b*. In addition, as shown in FIG. 8B, insulating member 2-3-*b* is provided on the outer circumference of unit electrode 1-3-*b*.

FIG. 8C is a cross-sectional view taken along the P3-P'3 line shown in FIG. 8A; FIG. 8C shows unit electrode 1-3-*c* of a device (an electric potential measuring device) after a wafer process is ended and then an assembly step is completed.

As shown in FIG. 8C, impurities 3-3-1-*c* and 3-3-2-*c* that have adhered from the environment are attached to surface U-3-*c* of unit electrode 1-3-*c*. In the left side of FIG. 8C, insulating member 2-3-1-*c* is stacked on the upper side of unit electrode 1-3-*c*, and covered region T-3-1-*c* of unit electrode 1-3-*c* is formed. In the right side of FIG. 7A, insulating member 2-3-4-*c* is provided on the upper side of unit electrode 1-3-*c* and on the right side surface of unit electrode 1-3-*c*. In more detail, insulating member 2-3-2-*c* is stacked on the upper side of unit electrode 1-3-*c* and covered region T-3-2-*c* of unit electrode 1-3-*c* is formed, and the right side surface of unit electrode 1-3-*c* is covered with insulating member 2-3-3-*c* so as to separate the right neighboring unit electrode 1-3-2-*c*. In addition, as shown in FIG. 8C, opened region S-3-*c* where the insulating members 2-3-1-*c* and 2-3-2-*c* are not stacked on the upper side of unit electrode 1-3-*c* is formed on unit electrode 1-3-*c*.

FIG. 8D is a cross-sectional view taken along the Q3-Q'3 line shown in FIG. 8B; FIG. 8D shows a manufactured unit electrode (readout electrode) 1-3-*d*.

As shown in FIG. 8D, impurities 3-3-1-*c* and 3-3-2-*c* are decomposed and ionized by the processing of electrochemical oxidation-reduction cycles, and impurities 3-3-1-*c* and 3-3-2-*c* can be removed. In the left side of FIG. 8D, insulating member 2-3-1-*d* is stacked on the upper side of unit electrode 1-3-*d*, and covered region T-3-1-*d* possessed by unit electrode 1-3-*d* is formed. In the right side of FIG. 8D, insulating member 2-3-4-*d* is provided on the upper side of unit electrode 1-3-*d* and on the right side surface of unit electrode 1-3-*d*. In more detail, insulating member 2-3-2-*d* is stacked on the upper side of unit electrode 1-3-*d* and covered region T-3-2-*d* possessed by unit electrode 1-3-*d* is formed, and the right side surface of unit electrode 1-3-*d* is covered with insulating member 2-3-3-*d* so as to separate the right neighboring unit electrode 1-3-2-*d*. In addition, as shown in FIG. 8D, opened region S-3-*d* where the insulating member is not stacked on the upper side of unit electrode 1-3-*d* is formed on unit electrode 1-3-*d*.

In addition, the surface of unit electrode 1-3-*d* (an action electrode) is oxidized and reduced by the processing of electrochemical oxidation-reduction cycles; thus, as shown in FIG. 8D, on the surface of opened region S-3-*d* of unit electrode 1-3-*d* (an action electrode), high portions and low portions are formed, and an uneven shape based on the high portions and the low portions is formed with surface U-3-*d* of unit electrode 1-3-*d* as a standard. In unit electrode 1-3-*d* (unit electrode 1-3-*b*), impurities are removed and an uneven shape is formed as compared to unit electrode 1-3-*c* (unit electrode 1-3-*a*); therefore, the surface area of unit electrode 1-3-*d* (unit electrode 1-3-*b*) is increased relative to the surface area of unit electrode 1-3-*c* (unit electrode 1-3-*a*); thus, the electrode impedance is lowered, and background noise in a case where electric potential is measured with a minute electrode array can be suppressed. The electric potential measuring device manufactured by using unit electrode 1-3-*d* (unit electrode 1-3-*b*) can two-dimensionally measure a feeble cell action potential, with high resolution and low noise.

5. Fourth Embodiment (Example 2 of Method for Manufacturing Electric Potential Measuring Device)

A method for manufacturing an electric potential measuring device according to a fourth embodiment of the present technology (example 2 of a method for manufacturing an electric potential measuring device) is a manufacturing method including stacking a metal member and an insulating member in this order on a readout electrode, forming, on the readout electrode, an opened region where the metal member and the insulating member are not stacked, and performing an electrochemical oxidation-reduction cycle on the readout electrode having the opened region. The electric potential measuring device manufactured by using the method for manufacturing an electric potential measuring device of the fourth embodiment according to the present technology can two-dimensionally measure a feeble cell action potential, with high resolution and low noise.

The method for manufacturing an electric potential measuring device of the fourth embodiment according to the present technology may include removing a substance attached to a surface of the opened region. Further, the method for manufacturing an electric potential measuring device of the fourth embodiment according to the present technology may include forming, on a surface of the opened region, at least one high portion with high height and/or at least one low portion with low height, with the stacking surface of the readout electrode with the insulating member as a standard, and may include forming, on a surface of the opened region, at least one high portion with high height with the stacking surface of the metal member with the insulating member as a standard. Furthermore, the method for manufacturing an electric potential measuring device of the fourth embodiment according to the present technology may include forming an uneven shape on a surface of the opened region.

A method for manufacturing an electric potential measuring device of the fourth embodiment according to the present technology will now be described using FIGS. 9A, 9B, 9C, 10A, 10B, 10C, and 10D. Note that an electric potential measuring device of the fourth embodiment according to the present technology can be manufactured by, except for the subject matter described in FIGS. 9A, 9B, 9C, 10A, 10B, 10C, and 10D, using a known method (for example, WO 2017/061171 A1).

Figure 9A:
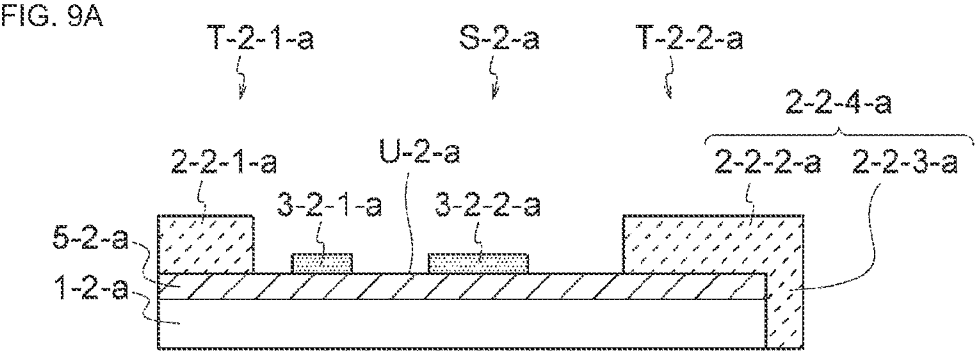
FIGS. 9A, 9B, and 9C are cross-sectional views showing an example of a method for manufacturing an electric potential measuring device of a fourth embodiment to which the present technology is applied.
Figure 9B:
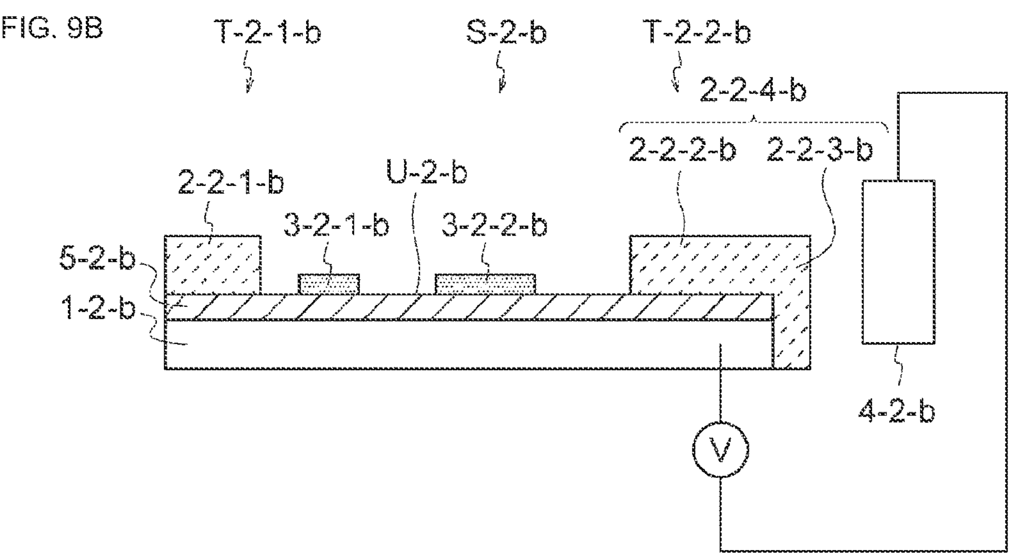
Figure 9C:
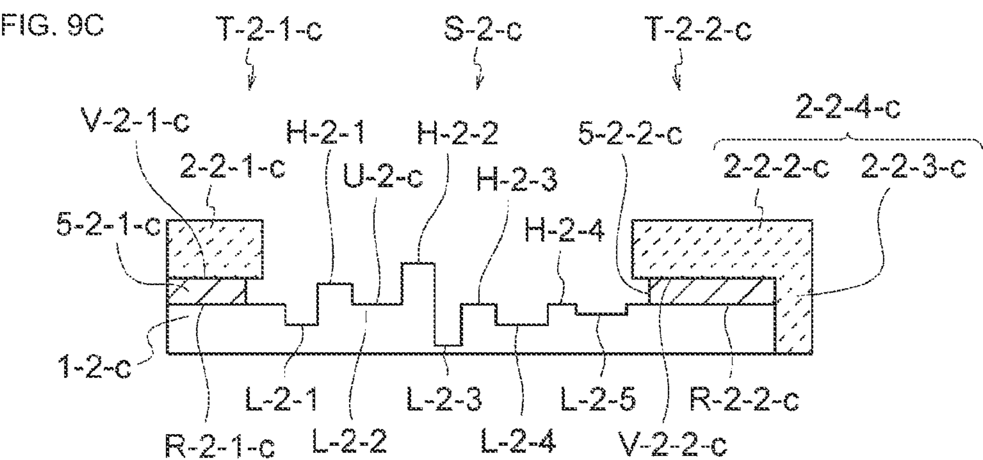

FIGS. 9A, 9B, and 9C are cross-sectional views showing an example of a method for manufacturing an electric potential measuring device according to the fourth embodiment of the present technology. FIGS. 10A, 10B, 10C, and 10D are top views and cross-sectional views showing an example of a method for manufacturing an electric potential measuring device according to the fourth embodiment of the present technology.

First, a method for manufacturing an electric potential measuring device of the fourth embodiment according to the present technology is described using FIGS. 9A, 9B, and 9C. FIG. 9A shows unit electrode 1-2-*a* of a device (an electric potential measuring device) after a wafer process is ended and then an assembly step is completed. Unit electrode 1-2-*a* (unit electrodes 1-2-*b* and 1-2-*c* in FIGS. 9B and 9C) is an action electrode, and may contain a noble metal electrode material. Examples of the noble metal electrode material include platinum, gold, iridium, rhodium, palladium, and the like. That is, it is sufficient that unit electrode 1-2-*a* be, for example, a platinum electrode or the like. Metal member 5-2-*a* is formed on unit electrode 1-2-*a*. Metal member 5-2-*a* (the metal members shown in FIGS. 9B and 9C described later) may contain, for example, a metal material with little harmfulness, a metal material with a large ionization tendency, etc.; examples of the metal material with little harmfulness include iron (Fe), magnesium (Mg), and the like. In a case where unit electrode 1-2-*a* is a platinum electrode and metal member 5-2-*a* is iron (Fe), immediately after platinum is sputtered, a metal with low biological harmfulness, such as iron, is continuously sputtered to a film thickness of, for example, 10 nm, and the workpiece is patterned; thus, a two-layer structure of unit electrode 1-2-*a* and metal member 5-2-*a* is formed.

As shown in FIG. 9A, impurities 3-2-1-*a* and 3-2-2-*a* that have adhered from the environment are attached to surface U-2-*a* of metal member 5-2-*a* stacked on unit electrode 1-2-*a*. In the left side of FIG. 9A, metal member 5-2-*a* and insulating member 2-2-1-*a* are stacked in this order on the upper side of unit electrode 1-2-*a*, and covered region T-2-1-*a* of unit electrode 1-2-*a* is formed. In the right side of FIG. 9A, insulating member 2-2-4-*a* is provided on the upper side of metal member 5-2-*a* stacked on the upper side of unit electrode 1-2-*a* and on the right side surfaces of unit electrode 1-2-*a* and metal member 5-2-*a*. In more detail, metal member 5-2-*a* and insulating member 2-2-2-*a* are stacked in this order on the upper side of unit electrode 1-2-*a* and covered region T-2-2-*a* of unit electrode 1-2-*a* is formed, and the right side surfaces of unit electrode 1-2-*a* and metal member 5-2-*a* are covered with insulating member 2-2-3-*a* so as to separate the right neighboring unit electrode (not illustrated) and the metal member (not illustrated). In addition, as shown in FIG. 9A, opened region S-2-*a* where the insulating member is not stacked on the upper side of unit electrode 1-2-*a* and metal member 5-2-*a* is stacked on the upper side of unit electrode 1-2-*a* is formed on unit electrode 1-2-*a*.

FIG. 9B is a diagram showing applying a potential difference between unit electrode (action electrode) 1-2-*b* and counter electrode 4-2-*b* in an electrolyte solution (for example, a physiological saline solution) to perform electrochemical oxidation-reduction cycles. For example, as shown in FIG. 9B, the electric potential of unit electrode (action electrode) 1-2-*b* is swept between 0 [V] and 3 [V] 30 times, with counter electrode 4-2-*b* as a standard. Counter electrode 4-2-*b* may be provided on a device of a minute electrode array, or separately a platinum electrode may be prepared and be used while being immersed in an electrolyte solution. As shown in FIG. 9B, impurities 3-2-1-*b* and 3-2-2-*b* that have adhered from the environment are attached to surface U-2-*b* of metal member 5-2-*b* stacked on unit electrode 1-2-*b*. In the left side of FIG. 9B, metal member 5-2-*b* and insulating member 2-2-1-*b* are stacked in this order on the upper side of unit electrode 1-2-*b*, and covered region T-2-1-*b* of unit electrode 1-2-*b* is formed. In the right side of FIG. 9B, insulating member 2-2-4-*b* is provided on the upper side of metal member 5-2-*b* stacked on the upper side of unit electrode 1-2-*b* and on the right side surfaces of unit electrode 1-2-*b* and metal member 5-2-*b*. In more detail, metal member 5-2-*b* and insulating member 2-2-2-*b* are stacked in this order on the upper side of unit electrode 1-2-*b* and covered region T-2-2-*b* of unit electrode 1-2-*b* is formed, and the right side surfaces of unit electrode 1-2-*b* and metal member 5-2-*b* are covered with insulating member 2-2-3-*b* so as to separate the right neighboring unit electrode (not illustrated) and the metal member (not illustrated). In addition, as shown in FIG. 9B, opened region S-2-*b* where the insulating member is not stacked on the upper side of unit electrode 1-2-*b* and metal member 5-2-*b* is stacked on the upper side of unit electrode 1-2-*b* is formed on unit electrode 1-2-*b*.

FIG. 9C shows a manufactured unit electrode (readout electrode) 1-2-*c*. As shown in FIG. 9C, impurities 3-2-1-*b* and 3-2-2-*b* are decomposed and ionized by the processing of electrochemical oxidation-reduction cycles described in FIG. 9B, and furthermore impurities 3-2-1-*b* and 3-2-2-*b* can be removed by lift-off using the melting of metal member 5-2-*b*. Note that the removal of impurities by lift-off can be used for a wide variety of impurities.

Like in the description in FIG. 2, in the left side of FIG. 9C, metal member 5-2-1-*c* and insulating member 2-2-1-*c* are stacked in this order on the upper side of unit electrode 1-2-*c*, and covered region T-2-1-*c* of unit electrode 1-2-*c* is formed. In the right side of FIG. 9C, insulating member 2-2-4-*c* is provided on the upper side of metal member 5-2-2-*c* stacked on the upper side of unit electrode 1-2-*c* and on the right side surfaces of unit electrode 1-2-*c* and metal member 5-2-2-*c*. In more detail, metal member 5-2-2-*c* and insulating member 2-2-2-*c* are stacked in this order on the upper side of unit electrode 1-2-*c* and covered region T-2-2-*c* of unit electrode 1-2-*c* is formed, and the right side surfaces of unit electrode 1-2-*c* and metal member 5-2-2-*c* are covered with insulating member 2-2-3-*c* so as to separate the right neighboring unit electrode (not illustrated) and the metal member (not illustrated). In addition, as shown in FIG. 9C, on unit electrode 1-2-*c*, the metal member 5-2-*b* which is not covered with insulating member 2-2-1-*b* or 2-2-2-*b* in the above manner is melted, and opened region S-2-*c* where the insulating member and the metal member are not stacked on the upper side of unit electrode 1-2-*c* is formed.

In addition, the surface of unit electrode 1-2-*c* (an action electrode) is oxidized and reduced by the processing of electrochemical oxidation-reduction cycles; thus, on the surface of opened region S-2-*c* of unit electrode 1-2-*c* (an action electrode), high portion H-2-1 and high portion H-2-2 with high height with stacking surface R-2-1-*c* of unit electrode 1-2-*c* with metal member 5-2-1-*c* and stacking surface R-2-2-*c* of unit electrode 1-1-*c* with metal member 5-2-2-*c* as a standard are formed, and high portion H-2-3 and high portion H-2-4 with substantially equal heights with stacking surface R-2-1-*c* and stacking surface R-2-2-*c* as a standard are formed. High portion H-2-2 is high also with the stacking surface V-2-1-*c* of unit electrode 1-2-*c* with insulating member 2-2-1-*c* and the stacking surface V-2-2-*c* of unit electrode 1-1-*c* with insulating member 2-2-2-*c* as a standard.

Further, on the surface of opened region S-1-*c* of unit electrode 1-2-*c* (an action electrode), low portion L-2-1, low portion L-2-2, low portion L-2-3, low portion L-2-4, and low portion L-2-5 with low height with stacking surface R-2-1-*c* of unit electrode 1-2-*c* with metal member 5-2-1-*c* and stacking surface R-2-2-*c* of unit electrode 1-1-*c* with metal member 5-2-2-*c* as a standard are formed.

The value obtained by adding up the positive volumes of high portions H-2-1 to H-2-4 with stacking surface R-2-1-*c* and stacking surface R-2-2-*c* as a standard (the positive amounts of the electrode material of the unit electrode) and the negative volumes of low portions L-2-1 to L-2-5 with stacking surface R-2-1-*c* and stacking surface R-2-2-*c* as a standard (the negative amounts of the electrode material of the unit electrode) is substantially zero. That is, the volume of unit electrode 1-2-*c* (the amount of the electrode material of the unit electrode) is substantially equal to the volume of a unit electrode that is substantially flat with stacking surface R-2-1-*c* and stacking surface R-2-2-*c* as a standard (for example, unit electrodes 1-2-*a* and 1-2-*b*) (the amount of the electrode material of the unit electrode). Further, on unit electrode 1-1-*c*, an uneven shape based on high portions H-1-1 to H-1-4 and low portions L-1-1 to L-1-5 is formed with surface U-1-*c* as a standard.

Thus, by removing impurities, the effective surface area of unit electrode 1-2-*c* (an action electrode) on which an uneven shape based on high portions H-2-1 to H-2-4 and low portions L-2-1 to L-2-5 is formed is increased relative to the surface area of a unit electrode that is substantially flat with stacking surface R-2-1-*c* and stacking surface R-2-2-*c* as a standard and to which impurities are attached (for example, unit electrodes 1-2-*a* and 1-2-*b*). By the increase of the surface area, the electrode impedance is lowered, and background noise in a case where electric potential is measured with a minute electrode array can be suppressed. The electric potential measuring device manufactured by using unit electrode 1-2-*c* can two-dimensionally measure a feeble cell action potential, with high resolution and low noise.

Next, a method for manufacturing an electric potential measuring device of the fourth embodiment according to the present technology is described using FIGS. 10A, 10B, 10C, and 10D. FIG. 10A is a top view of unit electrode 1-4-*a* of a device (an electric potential measuring device) after a wafer process is ended and then an assembly step is completed. Unit electrode 1-4-*a* (unit electrode 1-4-*b* in FIG. 10B) is an action electrode, and may contain a noble metal electrode material. Examples of the noble metal electrode material include platinum, gold, iridium, rhodium, palladium, and the like. That is, it is sufficient that unit electrode 1-4-*a* be, for example, a platinum electrode or the like. As shown in FIG. 10A, for example, impurities 3-4-1-*a* and 3-4-2-*a* that have adhered from the environment are attached to unit electrode 1-4-*a* via metal member 5-4-1-*a* stacked on unit electrode 1-4-*a*. That is, impurities 3-4-1-*a* and 3-4-2-*a* are attached to metal member 5-4-1-*a* directly. As shown in FIG. 10A, insulating member 2-4-*a* is provided on the outer circumference of unit electrode 1-4-*a*. Note that, since FIG. 10A is a top view, metal members 5-4-1-*c* and 5-4-2-*c* that are shown in FIG. 10C described later and that are stacked with insulating member 2-4-*s* are not illustrated.

FIG. 10B is a top view of a manufactured unit electrode (readout electrode) 1-4-*b*. As shown in FIG. 10B, impurities 3-4-1-*a* and 3-4-2-*a* are decomposed and ionized by the processing of electrochemical oxidation-reduction cycles and impurities 3-4-1-*a* and 3-4-2-*a* are removed, and an uneven shape based on high portions and low portions is formed on unit electrode (readout electrode) 1-4-*b*. In addition, as shown in FIG. 10B, insulating member 2-4-*b* is provided on the outer circumference of unit electrode 1-3-*b*. Note that, since FIG. 10B is a top view, metal members 5-4-1-*d* and 5-4-2-*d* that are shown in FIG. 10D described later and that are stacked with insulating member 2-4-*b* are not illustrated.

FIG. 10C is a cross-sectional view taken along the P4-P'4 line shown in FIG. 10A; FIG. 10C shows unit electrode 1-4-*c* of a device (an electric potential measuring device) after a wafer process is ended and then an assembly step is completed.

As shown in FIG. 10C, impurities 3-4-1-*c* and 3-4-2-*c* that have adhered from the environment are attached to surface U-4-*c* of metal member 5-4-1-*c* stacked on unit electrode 1-4-*c*. In the left side of FIG. 10C, metal member 5-4-1-*c* and insulating member 2-4-1-*c* are stacked in this order on the upper side of unit electrode 1-4-*c*, and covered region T-4-1-*c* of unit electrode 1-4-*c* is formed. In the right side of FIG. 10C, insulating member 2-4-4-*c* is provided on the upper side of metal member 5-4-1-*c* stacked on the upper side of unit electrode 1-4-*c* and on the right side surfaces of unit electrode 1-4-*c* and metal member 5-4-1-*c*. In more detail, metal member 5-4-1-*c* and insulating member 2-4-2-*c* are stacked in this order on the upper side of unit electrode 1-4-*c* and covered region T-4-2-*c* of unit electrode 1-4-*c* is formed, and the right side surfaces of unit electrode 1-4-*c* and metal member 5-4-1-*c* are covered with insulating member 2-4-3-*c* so as to separate the right neighboring unit electrode 1-4-2-*c* and the metal member 5-4-2-*c*. In addition, as shown in FIG. 10C, opened region S-4-*c* where the insulating members 2-4-1-*c* and 2-4-2-*c* are not stacked on the upper side of unit electrode 1-4-*c* and metal member 5-4-1-*c* is stacked on the upper side of unit electrode 1-4-*c* is formed on unit electrode 1-4-*c*.

FIG. 10D is a cross-sectional view taken along the Q4-Q'4 line shown in FIG. 10B; FIG. 10D shows a manufactured unit electrode (readout electrode) 1-4-*d*.

As shown in FIG. 10D, impurities 3-4-1-*c* and 3-4-2-*c* are decomposed and ionized by the processing of electrochemical oxidation-reduction cycles, and furthermore impurities 3-4-1-*c* and 3-4-2-*c* can be removed by lift-off using the melting of metal members 5-4-1-*c* and 5-4-2-*c*. Note that the removal of impurities by lift-off can be used for a wide variety of impurities.

In the left side of FIG. 10D, metal member 5-4-1-*d* and insulating member 2-4-1-*d* are stacked in this order on the upper side of unit electrode 1-4-*d*, and covered region T-4-1-*d* of unit electrode 1-4-*d* is formed. In the right side of FIG. 10D, insulating member 2-4-4-*d* is provided on the upper side of metal member 5-4-2-*d* stacked on the upper side of unit electrode 1-4-*d* and on the right side surfaces of unit electrode 1-4-*d* and metal member 5-4-2-*d*. In more detail, metal member 5-4-2-*d* and insulating member 2-4-2-*d* are stacked in this order on the upper side of unit electrode 1-4-*d* and covered region T-4-2-*d* of unit electrode 1-4-*d* is formed, and the right side surfaces of unit electrode 1-4-*d* and metal member 5-4-2-*d* are covered with insulating member 2-4-3-*d* so as to separate the right neighboring unit electrode 1-4-2-*d* and the metal member 5-4-3-*d*. In addition, as shown in FIG. 10D, on unit electrode 1-4-*d*, the metal member 5-4-1-*c* which is not covered with insulating member 2-4-1-*c* or 2-4-2-*c* in the above manner is melted, and opened region S-4-*d* where the insulating member and the metal member are not stacked on the upper side of unit electrode 1-4-*d* is formed.

In addition, the surface of unit electrode 1-4-*d* (an action electrode) is oxidized and reduced by the processing of electrochemical oxidation-reduction cycles; thus, on the surface of opened region S-4-*d* of unit electrode 1-4-*d* (an action electrode), high portions and low portions are formed, and an uneven shape based on the high portions and the low portions is formed with surface U-4-*d* as a standard. In unit electrode 1-4-*d* (unit electrode 1-4-*b*), impurities are removed and an uneven shape is formed as compared to unit electrode 1-4-*c* (unit electrode 1-4-*a*); therefore, the surface area of unit electrode 1-4-*d* (unit electrode 1-4-*b*) is increased relative to the surface area of unit electrode 1-4-*c* (unit electrode 1-4-*a*); thus, the electrode impedance is lowered, and background noise in a case where electric potential is measured with a minute electrode array can be suppressed. The electric potential measuring device manufactured by using unit electrode 1-4-*d* (unit electrode 1-4-*b*) can two-dimensionally measure a feeble cell action potential, with high resolution and low noise.

In addition, embodiments of the present technology are not limited to the above-described embodiments, and various alterations may occur insofar as they are within the scope of the present technology.

Note that the effects described in the present specification are merely examples, and not limitative; other effects may be exhibited.

Further, the present technology may also be configured as below.

[1]

An electric potential measuring device including:

a plurality of readout electrodes arranged in an array form and each configured to detect an electric potential of an action potential generation point generated by an action of a cell;

an insulating member;

a reference electrode configured to detect a reference potential; and an amplification section configured to obtain a potential difference between a detected electric potential based on the readout electrode and a detected electric potential based on the reference electrode, in which the readout electrode has a covered region where the insulating member is stacked on the readout electrode and an opened region where the insulating member is not stacked on the readout electrode, and the readout electrode has, in the opened region, at least one high portion with high height and/or at least one low portion with low height, with a stacking surface of the readout electrode with the insulating member as a standard.

[2]

The electric potential measuring device according to [1], in which an uneven shape is formed on a surface of the opened region.

[3]

An electric potential measuring device including:

a plurality of readout electrodes arranged in an array form and each configured to detect an electric potential of an action potential generation point generated by an action of a cell;

an insulating member;

a metal member;

a reference electrode configured to detect a reference potential; and an amplification section configured to obtain a potential difference between a detected electric potential based on the readout electrode and a detected electric potential based on the reference electrode, in which the readout electrode has a covered region where the metal member and the insulating member are stacked in this order on the readout electrode and an opened region where the metal member and the insulating member are not stacked on the readout electrode, and the readout electrode has, in the opened region, at least one high portion with high height and/or at least one low portion with low height, with a stacking surface of the readout electrode with the metal member as a standard.

[4]

The electric potential measuring device according to [3], in which the readout electrode has, in the opened region, at least one high portion with high height with a stacking surface of the metal member with the insulating member as a standard.

[5]

The electric potential measuring device according to [3] or [4], in which an uneven shape is formed on a surface of the opened region.

[6]

A method for manufacturing an electric potential measuring device, the method including:

stacking an insulating member on a readout electrode;

forming, on the readout electrode, an opened region where the insulating member is not stacked; and performing an electrochemical oxidation-reduction cycle on the readout electrode having the opened region.

[7]

The method for manufacturing an electric potential measuring device according to [6], the method further including: removing a substance attached to a surface of the opened region.

[8]

The method for manufacturing an electric potential measuring device according to [6] or [7], the method further including: forming, on a surface of the opened region, at least one high portion with high height and/or at least one low portion with low height, with a stacking surface of the readout electrode with the insulating member as a standard.

[9]

The method for manufacturing an electric potential measuring device according to any one of [6] to [8], the method further including: forming an uneven shape on a surface of the opened region.

[10]

A method for manufacturing an electric potential measuring device, the method including:

stacking a metal member and an insulating member in this order on a readout electrode;

forming, on the readout electrode, an opened region where the metal member and the insulating member are not stacked; and performing an electrochemical oxidation-reduction cycle on the readout electrode having the opened region.

[11]

The method for manufacturing an electric potential measuring device according to [10], the method further including: removing a substance attached to a surface of the opened region.

[12]

The method for manufacturing an electric potential measuring device according to [10] or [11], the method further including: forming, on a surface of the opened region, at least one high portion with high height and/or at least one low portion with low height, with a stacking surface of the readout electrode with the metal member as a standard.

[13]

The method for manufacturing an electric potential measuring device according to any one of [10] to [12], the method further including: forming, on a surface of the opened region, at least one high portion with high height with a stacking surface of the metal member with the insulating member as a standard.

[14]

The method for manufacturing an electric potential measuring device according to any one of [10] to [13], the method further including: forming an uneven shape on a surface of the opened region.

[15]

A method for manufacturing an electric potential measuring device, the method including: performing an electrochemical oxidation-reduction cycle on a readout electrode.

[16]

The method for manufacturing an electric potential measuring device according to [15], the method further including: removing a substance attached to a surface of the readout electrode.

[17]

The method for manufacturing an electric potential measuring device according to [15] or [16], the method further including: forming an uneven shape on a surface of the readout electrode.

REFERENCE SIGNS LIST

1, 21 Readout electrode
2 Insulating member
5 Metal member
14A Amplification section
22 Reference electrode
10 Electric potential measuring device
H High portion
L Low portion
T Covered region
S Opened region

The invention claimed is:

1. An electric potential measuring device comprising:

a plurality of readout electrodes in an array form, wherein each readout electrode of the plurality of readout electrodes is configured to detect an electric potential of an action potential generation point, and the electric potential is generated by an action of a cell;

an insulating member;

a reference electrode configured to detect a reference potential, wherein the reference electrode is within the array of the plurality of readout electrodes; and an amplification section configured to obtain a potential difference between the detected electric potential and the detected reference potential, wherein each readout electrode has a covered region and an opened region, the insulating member is present on the covered region of each readout electrode, the insulating member is absent on the opened region of each readout electrode, and each readout electrode has, in the opened region, at least one high portion with a first height and at least one low portion with a second height, the first height is higher than the second height with a stacking surface of a corresponding readout electrode with the insulating member as a standard.

2. The electric potential measuring device according to claim 1, wherein a shape of a surface of the opened region is uneven.

3. An electric potential measuring device comprising:

a plurality of readout electrodes in an array form, wherein each read electrode of the plurality of readout electrodes is configured to detect an electric potential of an action potential generation point, and the electric potential is generated by an action of a cell;

an insulating member;

a metal member;

a reference electrode configured to detect a reference potential, wherein the reference electrode is within the array of the plurality of readout electrodes; and an amplification section configured to obtain a potential difference between the detected electric potential and the detected reference potential, wherein each readout electrode has a covered region and an opened region, the metal member and the insulating member are present on the covered region of each readout electrode, the metal member and the insulating member are absent on the opened region of each readout electrode, and each readout electrode has, in the opened region, at least one high portion with a first height and at least one low portion with a second height, the first height is higher than second height with a stacking surface of a corresponding readout electrode with the insulating member as a standard.

4. The electric potential measuring device according to claim 3, wherein each readout electrode has, in the opened region, at least one portion with higher height with respect to a stacking surface of the metal member with the insulating member as a standard.

5. The electric potential measuring device according to claim 3, wherein a shape of a surface of the opened region is uneven.

6. A method for manufacturing an electric potential measuring device, the method comprising:

stacking an insulating member on a readout electrode;

forming, on the readout electrode, an opened region where the insulating member is not stacked;

performing an electrochemical oxidation-reduction cycle on the readout electrode having the opened region; and forming, on a surface of the opened region, at least one high portion with a first height and at least one low portion with a second height, wherein the first height is higher than the second height with a stacking surface of the readout electrode with the insulating member as a standard.

7. The method for manufacturing the electric potential measuring device according to claim 6, the method further comprising removing a substance attached to a surface of the opened region.

8. The method for manufacturing the electric potential measuring device according to claim 6, the method further comprising forming an uneven shape on a surface of the opened region.

9. A method for manufacturing an electric potential measuring device, the method comprising:

stacking a metal member and an insulating member in this order on a readout electrode;

forming, on the readout electrode, an opened region where the metal member and the insulating member are not stacked;

performing an electrochemical oxidation-reduction cycle on the readout electrode having the opened region; and forming, on a surface of the opened region, at least one high portion with a first height and at least one low portion with a second height, wherein the first height is higher than the second height with a stacking surface of the readout electrode with the metal member as a standard.

10. The method for manufacturing the electric potential measuring device according to claim 9, the method further comprising removing a substance attached to a surface of the opened region.

11. The method for manufacturing the electric potential measuring device according to claim 9, the method further comprising forming, on a surface of the opened region, at least one portion with a higher height with respect to a stacking surface of the metal member with the insulating member as a standard.

12. The method for manufacturing the electric potential measuring device according to claim 9, the method further comprising forming an uneven shape on a surface of the opened region.

* * * * *